United States Patent
Kringelum et al.

(10) Patent No.: US 9,289,003 B2
(45) Date of Patent: *Mar. 22, 2016

(54) USE OF COMPOUNDS INVOLVED IN BIOSYNTHESIS OF NUCLEIC ACIDS AS CRYOPROTECTIVE AGENTS

(75) Inventors: Børge Windel Kringelum, Ballerup (DK); Niels Martin Sørensen, Copenhagen SV (DK); Peter Sørensen, Ishøj (DK)

(73) Assignee: CHR. HANSEN A/S, Horsholm (DK)

( * ) Notice: Subject to any disclaimer, the term of this patent is extended or adjusted under 35 U.S.C. 154(b) by 1553 days.

This patent is subject to a terminal disclaimer.

(21) Appl. No.: 10/890,406

(22) Filed: Jul. 14, 2004

(65) Prior Publication Data

US 2005/0042594 A1 Feb. 24, 2005

Related U.S. Application Data

(63) Continuation-in-part of application No. 10/882,326, filed on Jul. 2, 2004, now abandoned, and a continuation-in-part of application No. PCT/DK2004/000477, filed on Jul. 2, 2004.

(60) Provisional application No. 60/484,126, filed on Jul. 2, 2003.

(30) Foreign Application Priority Data

Jul. 2, 2003 (EP) .................................. 03077079

(51) Int. Cl.
| | |
|---|---|
| *C12N 1/04* | (2006.01) |
| *A23C 17/02* | (2006.01) |
| *A23C 19/032* | (2006.01) |
| *C12N 1/38* | (2006.01) |

(52) U.S. Cl.
CPC ............... *A23C 17/02* (2013.01); *A23C 19/032* (2013.01); *C12N 1/04* (2013.01); *C12N 1/38* (2013.01)

(58) Field of Classification Search
USPC ......................................................... 435/260
See application file for complete search history.

(56) References Cited

U.S. PATENT DOCUMENTS

| | | | | |
|---|---|---|---|---|
| 5,756,315 | A * | 5/1998 | Mori et al. ....................... | 435/89 |
| 6,524,785 | B1 * | 2/2003 | Cozzone et al. ............... | 435/1.1 |
| 6,787,348 | B1 | 9/2004 | Kringelum et al. | |
| 7,732,184 | B2 | 6/2010 | Kringelum et al. | |
| 8,481,027 | B2 * | 7/2013 | Stavnsbjerg et al. ........ | 424/93.4 |
| 8,597,929 | B2 | 12/2013 | Kringelum et al. | |
| 2005/0042594 | A1 | 2/2005 | Kringelum et al. | |
| 2008/0171028 | A1 | 7/2008 | Kringelum et al. | |

FOREIGN PATENT DOCUMENTS

| | | |
|---|---|---|
| EP | 0259739 A1 | 3/1988 |
| EP | 1 493 806 | 1/2005 |
| EP | 1 644 481 | 10/2013 |
| JP | 50 071891 | 6/1975 |
| JP | 50071891 | * 6/1975 |
| JP | 05 308956 | 11/1993 |
| WO | WO 00/19817 | 4/2000 |
| WO | WO 00/39281 | 7/2000 |
| WO | WO 2006/072257 | 7/2006 |

OTHER PUBLICATIONS

Dahiya et al. "Growth of *Streptococcus* starter cultures in milk fortified with nucleic acid derivatives". J. Dairy Sci. 1964, 47(4), pp. 374-377.*
Gilliland et al. "Frozen concentrated cultures of lactic starter bacteria". J. Milk Food Technol. 1974. vol. 37, No. 2, pp. 107-111.*
Andersen et al., BIOKONSERVERING, Chr Hansen, Biblioteket, Jul. 3, 2001, pp. 28-29.
Chavarri et al., "Cryoprotective Agents for Frozen Concentrated Starters From Non-Bitter *Streptococcus lactis* Strains," Biotechnology Letters, vol. 10, No. 1, pp. 11-16, (1988).
Carcoba et al., "Influence of cryoprotectants on the viability and acidifying activity of frozen and freeze-dried cells of the novel starter strain *Lactococcus lactis* ssp. Lactis CECT 5180," Eur. Food Res. Technol. (2000) 211: 433-437, Springer-Verlag.
Database WPI, Section Ch, Week 199401, Derwent Publications Ltd., London GB; AN 1994-002160, XP002262355 & JP 05 308956 A (Mitsubishi Heavy Ind. Co Ltd), Nov. 22, 1993, Abstract.
Daszynski et al., "Storage of Erythrocytes at Temperatures –20 to 24° C.," Acta Med. Pol., 1981, 22, 2, pp. 151-160.
Adams et al., Food Microbiology, Second Edition, pp. 99-100, 2000, The Royal Society of Chemistry, Cambridge, U.K.
Mazur, "Physical and Temporal Factors Involved in the Death of Yeast at Subzero Temperatures," Biophysical Journal, vol. 1, 1961, pp. 247-264.
Font De Valdez et al., "Comparative Study of the Efficiency of Some Additives in Protecting Lactic Acid Bacteria against Freeze-Drying," Cryobiology 20, (1983), pp. 560-566, Academic Press Inc.
White, Principles of Biochemistry, International Student Edition, Nucleic Acids and Nucleoproteins, Chapter 9, pp. 184-187, McGrau-Hill, Inc., Published in Japan.
Alexander et al., American Type Culture Collection Methods, Laboratory Manual on Preservation Freezing and Freeze-Drying, Cryoprotective Additives, 1980, 8 pages.
Nielsen et al., Mejerilære, 1, 1999, pp. 172, Erhvervsskolemes Forlag, Odense.
Andersen, et al., Biokonservering, Ministeriet for Fødevarer, Landbrug og Fiskei, Veterinær-og Fødevaredirektoratet, Jul. 3, 2001, pp. 15-20.
Fonseca, et al., "Operating Conditions That Affect the Resistance of Lactic Acid Bacteria to Freezing and Frozen Storage," Cryobiology, Academic Press Inc., vol. 43, Nov. 2001, pp. 189-198.

(Continued)

*Primary Examiner* — Vera Afremova
(74) *Attorney, Agent, or Firm* — Hunton & Williams LLP

(57) ABSTRACT

A new type of cryoprotective agents that are useful for retaining the viability and metabolic activity of frozen or freeze-dried microbial cultures, is disclosed. The cryoprotective agent comprises compounds involved in biosynthesis of nucleic acids. Methods for the preparation as well as the uses of such cultures are given. Such cultures are useful as starter cultures in the manufacturing of food and feed products. Starter cultures of the invention include culture of lactic acid bacteria, e.g. *Lactococcus* species as well as other species.

24 Claims, 14 Drawing Sheets

(56) References Cited

OTHER PUBLICATIONS

Schmidt, et al., "Cryopreservation of Yeasts and Molds Cultures From Cheese Factories," Sciences des Aliments, vol. 11, No. 4, 1991, pp. 653-672.

Peter, et al., "The effect of growth phase, cryoprotectants and freezing rates on the survival of selected micro-organisms during freezing and thawing," Acta Alimentaria, vol. 30, No. 1, Mar. 2001, pp. 89-97.

Bekatorou, et al., "Low-temperature brewing by freeze-dried immobilized cells," Applied Biochemistry and Biotechnology—Part A Enzyme Engineering and Biotechnology, vol. 97, No. 2, 2002, pp. 105-121.

Ray, et al., "Freeze-Injury in Bacteria," CRC Critical Reviews in Clinical Laboratory Sciences, vol. 4, No. 2, Aug. 1973, pp. 161-213.

Koburger, et al. *J Bacteriol.* (1963) 85: 1051-1055.

Pine, et al. *Journal of Clinical Microbiology* (1986) 23(1): 163-169.

Bactéries Lactiques, Aspects fondamentaux et technologiques, vol. 1, H. de Roissart, F.M. Luquet, vol. 1 [1994] Chapter III-4, pp. 539-553, Lorica Chemin de Saint Georges.

Hughes & Hoover *J. Dairy Sci.* (1995) 78: 268-276.

Ishibashi, et al. *I.I.F-I.I.R.-Tokyo* (1985) 227-232.

* cited by examiner

USE OF COMPOUNDS INVOLVED IN BIOSYNTHESIS OF NUCLEIC ACIDS AS CRYOPROTECTIVE AGENTS

CROSS-REFERENCE TO RELATED APPLICATIONS

This application is a Continuation-in-Part of U.S. patent application Ser. No. 10/882,326, filed Jul. 2, 2004 now abandoned, which claims the benefit of U.S. Provisional Application No. 60/484,126, filed Jul. 2,2003, and European Patent Application No. EP 03077079.6, filed Jul. 2, 2003. This application is also a Continuation-In-Part of PCT Application No. PCT/DK2004/000477, filed Jul.2, 2004, entitled "USE OF COMPOUNDS INVOLVED IN BIOSYNTHESIS OF NUCLEIC ACIDS AS CRYOPROTECTIVE AGENTS. " The disclosures of each of the above-identified application are herein incorporated by reference in their entireties.

FIELD OF THE INVENTION

The invention relates to the field of frozen and freeze-dried microbial cultures and compounds involved in biosynthesis of nucleic acids as cryoprotective agents. More particularly the invention relates to cultures obtained by the use of such agents, which in addition to the cryoprotective activity, confer an increased metabolic culture activity when inoculated into the medium to be fermented or converted. Such frozen or freeze-dried cultures are useful in the manufacturing of numerous food and feed products.

BACKGROUND OF THE INVENTION

Microorganisms are involved in the manufacture of food and feed products including most dairy products. Bacterial cultures, in particular cultures of bacteria generally classified as lactic acid bacteria, are essential in the making of all fermented milk products, cheese and butter. However, cultures of certain non-bacterial microorganisms, e.g. certain yeasts and fungi, are used to process food and feed products. Cultures of these microorganisms are often referred to as starter cultures and impart specific features to various dairy products by performing a number of functions. Starter cultures are widely used in a variety of industries such as, the diary industry as well as in the wine manufacturing industry, and the juice manufacturing industry, the meat processing industry.

Cultures-of microorganisms also find important uses in the biopreservation of food-stuffs (Andersen et al., 1997).

Commercial dairy starter cultures are generally composed of lactose and citric acid fermenting bacteria. Lactic acid bacteria designate a group of Gram positive, non-motile, microaerophilic or anaerobic bacteria that ferment sugar with the production of acids including lactic acid. Industrially some of the most useful lactic acid bacteria include *Lactococcus* species, *Streptococcus* species, *Enterococcus* species, *Lactobacillus* species, *Leuconostoc* species and *Pediococcus* species.

Commonly used dairy starter culture strains of lactic acid bacteria are generally divided into mesophilic organisms having optimum growth temperatures at about 30° C. and thermophilic organisms having optimum growth temperatures in the range of about 35° C. to about 45° C. Examples of organisms belonging to the mesophilic group include *Lactococcus lactis* subsp. *lactis, Lactococcus lactis* subsp. *cremoris, Leuconostoc mesenteroides* subsp. *cremoris, Pediococcus pentosaceus, Lactococcus lactis* subsp. *lactis* biovar *diacetylactis* and *Lactobacilius paracasei* subsp. *paracasei.* Thermophilic lactic acid bacterial species include as examples *Streptococcus thermophilus, Enterococcus faecium, Lactobacillus delbrueckii* subsp. *lactis, Lactobacillus helveticus, Lactobacillus delbrueckii* subsp. *bulgaricus* and *Lactobacillus acidophilus.*

Dairy starter cultures are also classified according to their specific species composition and preferred industrial use. A pure starter culture comprises only a single specie whereas a mixed culture comprises two or more different species. Starter cultures are often categorized according to the temperature at which they display optimal growth or maximal enzymatic activity. Mesophilic starter cultures typically have an optimum temperature of about 30° C., whereas thermophilic cultures have an optimum temperature of about 35-45° C. (Nielsen and Ullum, 1999). Examples of commercial mesophilic mixed cultures include:

"O-culture" comprising *Lactococcus lactis* subsp. *lactis* and *Lactococcus lactis* subsp. *cremoris.*

"D-culture" comprising *Lactococcus lactis* subsp. *lactis, Lactococcus lactis* subsp. *cremoris* and *Lactococcus lactis* subsp. *lactis* biovar *diacetylactis.*

"L-culture" comprising *Lactococcus lactis* subsp. *lactis, Lactococcus lactis* subsp. *cremoris* and *Leuconostoc* species.

"LD-culture" comprising *Lactococcus lactis* subsp. *lactis, Lactococcus lactis* subsp. *cremoris, Lactococcus lactis* subsp. *lactis* biovar *diacetylactis* and *Leuconostoc* species.

An O-culture is used to make cheese without holes (Cheddar, Cheshire, Feta). A D-culture is used to make butter. A L-culture is used to make cheese with smallholes (e.g., cottage cheese) and curdled milk products with low $CO_2$-production. A LD-culture is used to make cheese with normal hole sizes, curdled milk products (junket) and sour butter. Commercially, LD-cultures are currently one of the most used mixed cultures.

Examples of commercial thermophilic mixed cultures include:

"Yoghurt culture" comprising *Streptococcus thermophilus* and *Lactobacillus delbrueckii* subsp. *bulgaricus,* and "Thermophilic cheese culture" comprising *Streptococcus thermophilus* and *Lactobacillus helveticus.*

A Yoghurt culture is used to make yoghurt and special Italian cheeses, Thermophilic cheese culture is used to make Emmentaler cheese and special Italian cheeses.

In addition, species of *Propionibacterium* are frequently used as dairy starter cultures, particularly in the manufacture of cheese. Also organisms belonging to the *Brevibacterium* genus and the *Bifidobacterium* genus are commonly used as food starter cultures.

Another group of microbial starter cultures is fungal cultures, including yeast cultures and cultures of filamentous fungi, which are useful in the manufacture of certain types of cheese and beverage. Examples include *Penicillium roqueforti, Penicillium candidum, Geotrichumcandidum, Torula kefir, Saccharomyces kefir* and *Saccharomyces cerevisiae.*

Starter cultures are also widely used in the meat processing industry, e.g. for the manufacturing of various .sausages and salamis.

Commercial starter cultures are commonly be distributed as frozen cultures. At the low temperature the frozen cultures, most metabolic activities in the cell cease and cells can be maintained in this suspended, but viable, state for extended periods.

Concentrated frozen cultures are commercially very interesting since the cultures can be inoculated directly. into the, production container. By using concentrated frozen cultures the end-user avoids the otherwise obligatory, time-consuming intermediary fermentation step during which the starter culture is amplified, and the end-user reduces the risk of contamination significantly. Concentrated cultures, may be referred to as DVS—direct vat set™ cultures.

As an alternative to concentrated frozen cultures, concentrated freeze-dried DVS™ cultures may be prepared. These cultures have an additional advantage in that they can be shipped without refrigeration.

In general, possible damaging effects of freezing and thawing on the viability of living cells has been ascribed to cell dehydration and the formation of ice crystals in the cytosol during freezing.

A number of cryoprotective agents have been found to effect the concentration of the cytosol in a controlled and minimally injurious manner so that ice crystallization in the cytosol is precluded or minimized during freezing.

An article by F. J. Chavarri et al. (Biotechnology letters, vol 10, 1, 11-16 (1988), "Cryoprotective agents for frozen concentrated starters from non-bitter *Streptococcus Lactis* strains") describes the storage viability of a frozen pure *Streptococcus lactis* culture may be improved by addition of 5% lactose or 5% sucrose. The lactose or sucrose worked as cryoprotective agents. *Streptococcus lactis* is a former name of *Lactococcus lactis* subsp. *lactis*.

Similarly, an article by R. Cárcoba et al (Eur Food Res Technol (2000) 211,433 -437, "Influence of cryoprotectants on the viability and acidifying activity of frozen and freeze-dried cells of the novel starter strain *Lactococcus lactis* subsp. *lactis* CECT 5180") describes that storage viability of a frozen pure *Lactococcus lactis* subsp. *lactis* culture could be improved by addition of different cryoprotective agents such as sugars (lactose, sucrose and trehalose), glutamic acid and gelatine.

The viability of freeze-dried cultures may also be improved by use of cryoprotective agents. For instance EP259739 describes a number of different cryoprotective agents for freeze-dried cultures.

There have been various approaches to provide cryoprotection such as carbonhydrates, proteins and certain surface active agents.

In general relatively large amounts of cryoprotective agents are required in order to obtain the cryoprotective effect. While this presents an insignificant problem in some settings, it presents a significant problem for food processing industries where even a small undesired deviation in the taste of the fermented or processed product that is caused by the cryoprotective agent can be detrimental. We are not aware of any commercial available concentrated frozen cultures that contain significant amounts of cryoprotective agents.

Agents other than carbonhydrates, proteins and surface-active agents have been used to improve the stability of cultures at low temperature.

WO 00/39281 describes the use of IMP and compounds involved in the biosynthesis of DNA synthesis to stabilize the metabolic activity of a liquid starter cultures, rather than the stability of frozen or freeze-dried cultures.

WO 00/19817 describes a cryoprotective composition, in which a combination compounds rather than any single component is used for cryoprotection. The combination includes a calcium channel blocker, a cell nutrient matrix, water and adenosine. However, the use of pharmaceutical active compounds such as calcium channel blockers are not acceptable for food industry applications.

JP 05 308956 describes a culture medium for the culture of nitrite bacteria that comprises a high molecular polysaccharide in which a unit consisting of 1 molecule of alpha-Lrhamnose, 1 molecule of D-glucuronic acid and 2 molecules of D-glucose polymerized linearly and e.g. ATP. Nitritate bacteria cultured in this medium can be frozen and stored. There is no indication that components of the medium may function as a cryoprotective agent when added to concentrated cultures prior to freezing.

The need remains for effective cryoprotective agents that can be added to concentrated cultures used in the food industry.

SUMMARY OF THE INVENTION

It was believed there were no significant storage stability problems for commercially relevant concentrated frozen lactic acid bacteria cultures. Although it is well known that most living cells suffers from freezing and the subsequent thawing, the issue of viability was generally not considered of significant for commercially relevant concentrated frozen lactic acid bacteria cultures. Consequently commercially available concentrated frozen cultures do not have significant amounts of cryoprotective agents. This may be because some commercial starter cultures seem to be very resistant to the damaging effects of freezing and thawing.

For instance, a number of stability studies were performed with commercial concentrated lactic acid bacteria cultures that had been frozen for 2-3 months. The 2-3 month old frozen cultures showed no significant degradation of culture activity over a period of one year at temperature below −45° C. Consequently, it was believed that commercially relevant cultures did not have significant storage stability problems.

The present inventors observed for instance that frozen LD-cultures have a significant loss of activity within the first 1-3 weeks of frozen storage (as illustrated in example 1). After the first few weeks further loss of activity was relatively insignificant and in line with the prior known results described above.

The inventors identified unrecognised stability problems relate to the freezing and the initial phase of storage for some types of commercially relevant concentrated frozen lactic acid bacteria cultures, e.g. commercial available frozen LD-cultures. Particularly, when the cultures are stored at the temperature provided by modern industrial freezers, typically around −50° C.

The inventors have identified a new class of cryoprotective agents that address both the problem of stability and confer an increased metabolic activity of the culture.

One embodiment of the invention relates to a concentrated frozen or freeze-dried culture, wherein the culture comprises one or more cryoprotective agent(s) selected from the group consisting of one or more compound(s) involved in the biosynthesis of nucleic acids or one or more derivative(s) of any such compounds, The cryoprotective agent is preferably added to the viable bacteria before they are frozen or freeze dried.

The present invention also provides a method for making a frozen culture or a freeze dried culture comprising the following steps: adding one or more cryoprotective agent(s) selected from the group consisting one or more compound(s) involved in the biosynthesis of nucleic acids or one or more derivative(s) of any such compounds to viable organisms; freezing the material to get frozen material, and packing the frozen (or freeze dried) material in a suitable way. In the case of making a freeze dried culture the method comprises a step where sublimation of water from the frozen material occurs prior to the packing step.

According to the present invention, there is also provided a method of preparing a food and a feed product, which comprises the usage of a culture according to the invention. Preferably the food product is selected from a milk-based product, a meat product, a vegetable product and a beverage.

A further advantage of the herein described new class of cryoprotective agents is that they retain the viability as well as the metabolic activity of the reconstituted cells and do not affect the taste of the fermented or processed product in any adverse way.

Deffinitions

Prior to a discussion of the detailed embodiments of the invention is provided a definition of specific terms related to the various aspects and embodiments of the invention.

As used herein the term "lactic acid bacterium" (LAB) designates a gram-positive, microaerophilic or anaerobic bacterium, which ferments sugars with the production of acids including lactic acid (as the predominantly produced acid), acetic acid and propionic acid. The industrially most useful lactic acid bacteria are found among *Lactococcus* species (spp.), *Streptococcus* spp., *Lactobacillus* spp., *Leuconostoc* spp., *Pediococcus* spp., *Brevibacterium* spp, *Enterococcus* spp. and *Propionibacterium* spp. Additionally, bacteria belonging to the group of the strict anaerobic bacteria, *bifidobacteria*, i.e. *Bifidobacterium* spp. which are frequently used as food starter cultures alone or in combination with lactic acid bacteria, are generally included in the group of lactic acid bacteria.

By the term a "concentrated" culture is referred to a composition that have a content of viable cells (colony forming units, CFUs) which is at least $10^8$ CFU per ml, more preferably at least $10^9$ CFU per ml, more preferably at least $10^{10}$ CFU per ml, more preferably at least $10^{11}$ CFU per ml, or more preferably at least $10^{12}$ CFU per ml. As can be seen in the examples a concentrated culture may for instance be obtained by centrifugation.

The term "packing" should be understood broadly. It denotes that the frozen or freeze-dried culture is packed in a manner that may be provided to the user. It may be packed in a bottle, a tetra-pack®, a bag, etc.

The term "a cryoprotective agent" denotes a substance that is able to improve the resistance of the damaging effects induced by freezing and the initial phase of the storage of a frozen or freeze-dried culture. In the present context it may be a single specific cryoprotective agents or it may be two or more different agents. Accordingly, the w/w percentage of the cryoprotective agent(s) within the culture material should be understood as the sum of the amount of cryoprotective agent(s). A preferred way to determine whether a substance is a cryoprotective agent that is able to improve resistance of the frozen culture to the damaging effects induced by freezing and the initial phase of the storage, is to spilt a culture, as described herein, into two samples, adding a specified amount of the cryoprotective agent to one of them, freezing both of them and measuring the acidifying activity in the relevant media (e.g. milk) of the cultures on the same day as freezing and periodically (e.g. up to one year) when kept under frozen storage. If the culture with cryoprotective agent has improved activity seen over the storage period: (such as improved milk-acidifying activity) the substance is a cryoprotective agent. A suitable milk acidifying activity assay is given in working examples herein.

Embodiments of the present invention are described below, by way of examples only.

DETAILED DISCLOSURE OF THE INVENTION

As discussed previously, concentrated frozen of freeze-dried cultures are considered to be stable. However contrary to the general belief in the. field the inventors surprisingly observed hitherto unrecognised stability problems related to the freezing and the initial phase of the storage for some types of commercially relevant concentrated frozen lactic acid bacteria cultures, such as e.g. commercially available frozen LD-cultures, see Example. 1 below. It is contemplated that such stability problems will be widely found when commercially frozen or freeze-dried cultures are tested appropriately.

In order to overcome this problem a number of possible agents were tested to see if they could overcome the problem. Among the agents tested were agent(s) selected from the group consisting one or more compound(s). involved in the biosynthesis of nucleic acids which previously were shown by the inventors to improve the stability. of non-frozen, liquid starter cultures.

WO 00/39281 describes the use of IMP and compounds involved in the biosynthesis of DNA synthesis to stabilize the. metabolic activity of a liquid starter cultures, but contrary to cultures, which remain liquid during cooling, cultures that freeze are subjected to a number of potential damaging issues that relates directly to the freezing process.

At the freezing temperature, microorganisms are subjected to death and injury as the culture begins to freeze and ice is formed both extra- and intracellularly. The ice formation imposes mechanical damage to cells and furthermore generates high extra cellular osmotic pressures that will dehydrate the cells. Changes in the ionic strength and pH of the water phase as a result of freezing will also disrupt the structure and function of numerous cell components and macromolecules which depend on these factors for their stability (Adams, 2000).

The difference between the stability issues of liquid versus frozen cultures can further be illustrated by an experiment reported by Mazur (1961). In this experiment Yeasts cells were immersed in a bath at $-15°$ C. The result was that 97% of the cells survived when the system remained liquid, but only 27% of the cells survived when that external medium froze at $-15°$ C. (Mazur 1961)

Therefore the measures that have to be provided by an effective cryoprotective agent are very much different depending on whether the cryoprotective agent is designed to protect liquid or frozen cultures, and consequently, additives, which are effective cryoprotective agents of liquid cultures, may not be effective for frozen cultures. One example of such an additive is Na-formate. As reported in WO 00/39281 3% Na-formate is effective to increase the storage stability of liquid lactic acid-bacterial starter culture concentrates. However, as illustrated in Example 15 below, 3% Na-formate decrease the storage stability of frozen lactic acid bacterial starter culture.

It was therefore completely surprising when experiments showed that IMP and certain compound(s) involved in the biosynthesis of nucleic acids improved the stability of both frozen and freeze dried concentrated cultures.

As it is shown in Example 2 below, the addition of one such compound, inosine-5'-monophosphate (IMP), significantly improves the resistance of the damaging effects induced by freezing and the initial phase of the storage. The addition of IMP also significantly improves the stability of a freeze-dried culture as illustrated in example 9 below. From example 10 below it is clear that not only IMP, but a wider range of agents selected from the group consisting of compound(s) involved in the biosynthesis of nucleic acids are effective as cryoprotective agents.

As illustrated in example 10 both nucleotides and nucleosides can be used as cryoprotective agents. Thus, in preferred embodiments, a cryoprotective compound which is useful to improve the resistance of the damaging effects induced by freezing and the initial phase of the storage of a starter culture is a compound selected from the group comprising a compound involved in the biosynthesis of nucleic acids, including the group of purine bases, pyrimidine bases, nucleosides and nucleotides. In another preferred embodiment, a cryoprotective compound which is useful to improve the resistance of the damaging effects induced by freezing and the initial phase of the storage of a starter culture is a compound comprising a compound involved in the biosynthesis of nucleic acids or one or more derivative(s) of any such compound. In another preferred embodiment, a cryoprotective compound which is useful to improve the resistance of the damaging effects induced by freezing and the initial phase of the storage of a starter culture is a compound comprising one or more purine bases, one or more pyrimidine bases, one or more nucleosides or one or more nucleotides, including combinations thereof. In another embodiment of the invention, a cryoprotective compound which is useful to improve the resistance of the damaging effects induced by freezing and the initial phase of the storage of a starter culture is selected from the group consisting of purine bases, pyrimidine bases, nucleosides and nucleotides. Such compounds are exemplified by inosine-5'-monophosphate (IMP), adenosine-5'-monophosphate (AMP), guanosine-5'-monophosphate (GMP), uranosine-5'-monophosphate (UMP), cytidine-5'-monophosphate (CMP), adenine, guanine, uracil, cytosine, guanosine, uridine, cytidine, hypoxanthine, xanthine, hypoxanthine, orotidine, thymidine, inosine and a derivative of any of such compounds or mixtures thereof. The invention also contemplates a frozen or freeze-dried culture comprising one or more cryoprotective agent(s) comprising one or more compounds involved in the biosynthesis of nucleic acids or one or more derivative(s) of any such compound. In another embodiment of the invention, the frozen or freeze-dried culture comprises one or more cryoprotective agents comprising one or more purine bases, one or more pyrimidine bases, one or more nucleosides or one or more nucleotides, including one or more combinations thereof. In another embodiment of the invention, the frozen or freeze-dried culture comprises one or more cryoprotective agents selected from the group consisting of purine bases, pyrimidine bases, nucleosides and nucleotides.

As described earlier WO 00/19817 provides a combination of a calcium channel blocker, a cell nutrient matrix, water and adenosine as a cryoprotective composition, however, the possible cryoprotective activity of single components, such as e.g. adenosine was not discussed. However, adenosine may not be effective as a cryoprotective agent, as illustrated in example 12 and 15, wherein adenosine appears to decrease the stability of bacterial cultures. Further, Demetriou (WO 00/19817) used amounts of 2.7 to 3.6 mM adenosine. Additionally, our experiments show that inosine is very effective as a cryoprotective agent and both adenosine and inosine are purine nucleotides. This observation can be extended to the monophosphates. Our experiments show that IMP, but not AMP is effective as a cryoprotective agent. This is even more surprising since, in the organism, inosinic acid (IMP) is synthesized from adenylic acid (AMP) by hydrolytic deamination (White, 1973). Thus in a preferred embodiment of the invention the one or more cryoprotective agent(s) is/are selected from the group of pyrimidine nucleotides and inosine.

In a further preferred embodiment of the invention the one or more cryoprotective agent(s) is/are selected from the group of nucleoside monophosphates. In another preferred embodiment of the invention, the one or more cryoprotective agent(s) comprises nucleoside monophosphates. In a preferred embodiment at least one or the only cryoprotective agent is IMP.

Carbonhydrate or proteinaous type cryoprotectant agents are not in general described to increase the metabolic activity of thawed or reconstituted cultures. The cryoprotective agents of the invention may in addition to their cryoprotective activity also confers an increased metabolic activity (booster effect) of the culture when it is inoculated into the medium to be fermented, processed or converted.

Thus one embodiment of the invention is a frozen or freeze-dried culture, wherein the cryoprotective agent is an agent or mixture of agents, which in addition to its cryoprotectivity has a booster effect.

The expression "booster effect" is used to describe the situation wherein the cryoprotective agent confers an increased metabolic activity (booster effect) on to the thawed or reconstituted culture when it is inoculated into the medium to be fermented or converted. Viability and metabolic activity are not synonymous concepts. Commercial frozen or freeze-dried cultures may retain their viability, although they may have lost a significant portion of their metabolic activity e.g. cultures may lose their acid-producing (acidification) activity when kept stored even for shorter periods of time. Thus viability and booster effect has to be evaluated by different assays. Whereas viability is assessed by viability assays such as the determination of colony forming units, booster effect is assessed by quantifying the relevant metabolic activity of the thawed or reconstituted culture relative to the viability of the culture. The acidifying activity assay described below is one example of an assay quantifying the relevant metabolic activity of the thawed or reconstituted culture. The booster effect is further illustrated in Example 3.

Although the acid-producing activity is exemplified herein, this invention is intended to encompass the stabilization of any types of metabolic activities of a culture. Thus, the term "metabolic activity" refers to the oxygen removal activity of the cultures, its acid-producing activity, i. e. the production of e. g. lactic acid, acetic acid, formic acid and/or propionic acid, or its metabolite producing activity such as the production of aroma compounds such as acetaldehyde, ($\alpha$-acetolactate, acetoin, diacetyl and 2,3-butylene glycol (butanediol)).

In an embodiment of the invention the frozen culture contains or comprises from about 0.2% to about 20% of the cryoprotective agent or mixture of agents measured as % w/w of the frozen material. It is, however, preferable to add the cryoprotective agent or mixture of agents at an amount which is in the range from 0.2% to 15%, more preferably within the range of 0.2% to 10%, more preferably within the range of 0.5% to 7%, and more preferably within the range of 1% to 6% by weight, including within the range of 2% to 5% of the cryoprotective agent or mixture of agents measured as % w/w of the frozen material by weight. In a preferred embodiment the culture comprises approximately 3% of the cryoprotective agent or mixture of agents measured as % w/w of the frozen material by weight. The preferred amount of approximately 3% of the cryoprotective agent corresponds to concentrations in the. 100 mM range. It should be recognized that for each aspect of embodiment of the invention the ranges may be increments of the described ranges.

The term "material" of the culture denotes the relevant substances of the culture including both the viable bacteria and cryoprotective agent. Possible packing is not included. Consequently, the weight of the material of the culture does not include the weight of possible packing.

In the case that the culture is a freeze-dried culture it is preferred to add the cryoprotective agent or mixture of agents at an amount, which is in the range of 0.8% to 60% by weight, or within the range of 0.8% to 55% by weight, or within the range of 1.3% to 40% by weight, or within the range of 3% to 30% by weight, or within the range of 6% to 25% by weight, including the range of 10% to 24% by weight. In a preferred embodiment the freeze-dried culture comprises approximately 16% of the cryoprotective agent or mixture of agents measured as % w/w of the freeze-dried material by weight.

Additionally, the frozen or freeze-dried culture may contain further conventional additives including nutrients such as yeast extract, sugars, antioxidants, inert gases and vitamins etc. Also surfactants including Tween® compounds can be used as further additive to the culture according to the invention.

Further examples of such conventional additives, which in addition may be added to the culture according to the invention, may be selected from proteins, protein hydrolysates and amino acids. Preferred suitable examples of these include the ones selected from the group consisting of Glutamic acid, Lysine, Na-glutamate, Na-caseinate, Malt extract, Skimmed milk powder, Whey powder, Yeast extract, Gluten, Collagen, Gelatin, Elastin, Keratin, and Albumins or mixtures thereof.

More preferably the conventional additives is a carbonhydrate. Suitable examples of these include the ones selected from the group consisting of Pentoses (eg. Ribose, Xylose), Hexoses (e.g. fructose, mannose, Sorbose), Disaccharides (eg. Sucrose, Trehalose, Melibiose, Lactulose), Oligosaccharides (e.g. Raffinose), Oligofrutoses (eg. Actilight, Fribroloses), Polysaccharides (e.g. Maltodextrins, Xanthan Gum, Pectin, Alginate, Microcrystalline cellulose, Dextran, PEG), and Sugar alcohols (Sorbitol, Manitol and Inositol).

Although the present invention relates to any concentrated frozen of freeze dried cultures, it is in particular directed to cultures of microorganisms that are involved in the manufacture of food and feed products including, most dairy products. Preferred embodiments of the invention comprise bacterial cultures, in particular cultures of bacteria that are generally classified as lactic acid bacteria and which are essential in the making of all fermented milk products, cheese and butter. Cultures of such bacteria are often referred to as starter cultures and they impart specific features to various dairy products by performing a number of functions. However also cultures that comprise fungal cultures, including yeast cultures and cultures of filamentous fungi, which are particularly used in the manufacture of certain types of cheese and beverage, are referred to as starter cultures. Also cultures, which are used to process other types of food or feed products, are referred to as starter cultures. The cultures used in the manufacturing of silage are often referred to as starter cultures too.

In accordance with the invention, any starter culture organism that is of use in the food or feed industry including the dairy industry can be used. Thus, the starter culture can comprises one or more organisms selected from the group comprising a lactic acid bacterial (LAB) spp., a *Bifidobacterium* spp., a *Brevibacterium* spp., a *Propionibacterium* spp. or a fungal spp. such as a *Torula* spp., a *Penicillium* spp., a *Cryptococcus*. spp., *Debraryomyces* spp., *Klyveromyces* spp. and a *Saccharomyces* spp.. Suitable cultures of the lactic acid bacterial (LAB) group include commonly used strains of a *Lactococcus* spp., a *Streptococcus* spp., a *Lactobacillus* spp. including the *Lactobacillus acidophilus, Enterococcus* spp., *Pediococcus* spp., a *Leuconostoc* spp., *Oenococcus* spp.. *Lactococcus* spp. and include the widely used *Lactococcus lactis*, including *Lactococcus lactis* subsp. *lactis* and *Lactococcus lactis* subsp. *cremoris* which are commonly used in the manufacture of cheeses with a closed texture, e. g. Cheddar, Feta and cottage cheese.

In another embodiment of the invention, the starter culture comprises one or more organisms comprising a lactic acid bacterial (LAB) spp., a *Bifidobacterium* spp., a *Brevibacterium* spp., a *Propionibacterium* spp. or a fungal spp. such as a *Torula* spp., a *Penicillium* spp., a *Cryptococcus* spp., *Debraryomyces* spp., *Klyveromyces* spp. and a *Saccharomyces* spp.. Suitable cultures of the lactic acid bacterial (LAB) group include commonly used strains of a Lactococcus spp., a *Streptococcus* spp., a *Lactobacillus* spp. including the *Lactobacillus acidophilus, Enterococcus* spp., *Pediococcus* spp., a *Leuconostoc* spp., *Oenococcus* spp.. *Lactococcus* spp. and include the widely used *Lactococcus lactis*, including *Lactococcus lactis* subsp. *lactis* and *Lactococcus lactis* subsp. *cremoris* which are commonly used in the manufacture of cheeses with a closed texture, e. g. Cheddar, Feta and cottage cheese.

It will be appreciated, that the starter culture organism can be selected from a genetically modified strain of one or more of the above lactic acid bacterial strains or any other starter culture strains. As used herein the expression "genetically modified bacterium" is used in the conventional meaning of that term i.e. it refers to strains obtained by subjecting a bacterial strain to any conventionally used mutagenization treatment including treatment with a chemical mutagen such as ethanemethane sulphonate (EMS) or Nmethyl-N'-nitro-N-nitroguanidine (NTG), to UV light or to spontaneously occurring mutants, including classical mutagenesis. Furthermore it is possible to provide the genetically modified bacterium by random mutagenesis followed by selection of the spontaneously occurring mutants, i.e. without the use of recombinant DNA-technology. It is further envisaged that mutants of lactic acid bacteria and other potential useful starter culture organisms can be provided by such technology including site-directed mutagenesis and PCR techniques and other in vitro or in vivo modifications of specific DNA sequences once such sequences have been identified and isolated. Thus it is further contemplated that useful starter culture organisms can be obtained by use of recombinant DNA-technology. In particular the possibility to obtain useful starter culture organisms by recombination of DNA-sequences that were inherent to the particular organism, i.e. self-cloning, is attractive from a food-regulation point of view.

As it is usual in the dairy industry, the starter: culture may comprise a mixture of strains including a mixture of strains of different lactic acid bacterial species, such as e. g. a mixture of *Streptococcus thermophilus* and *Lactobacillus delbrueckii* subsp. *bulgaricus.*

Commonly used dairy starter culture strains generally divided into "mesophilic organisms", which in the present context is organisms having optimum growth temperatures at about 30° C. and "thermophilic organisms", which in the present context is organisms having optimum growth temperatures in the range of about 40 to about 45° C.

The selection of strains for the starter culture of the invention will depend on the particular type of fermented food or feed product to be manufactured. E.g. for cheese and butter manufacturing, mesophilic cultures of *Lactococcus* species, *Leuconostoc* species and *Lactobacillus* species are widely used. Thus in one embodiment the culture according to the invention comprises one or more mesophilic organisms having optimum growth temperatures at about 30° C. Typical organisms belonging to such mesophilic organisms include *Lactococcus lactis, Lactococcus lactis* subsp. *cremoris, Leuconostoc mesenteroides* subsp. *cremoris, Pediococcus pen-* tosaceus, *Lactococcus lactis* subsp. *lactis* biovar *diacetylactis, Lactobacillus casei* and *Lactobacillus paracasei* subsp. *paracasei*.

In yet another embodiment of the invention the culture according to the invention comprises one or more thermophilic organism(s) having optimum growth temperatures at about 40° C. to about 45° C. Thermophilic organisms are frequently used to produce yoghurt and other fermented milk products, but also certain cheese are produced by use of thermophilic cultures, e.g. emmentaler cheese and special Italian cheeses. Typical organisms belonging to such Thermophilic organisms include organisms selected from the group comprising *Streptococcus thermophilus, Enterococcus faecium, Lactobacillus delbrueckii* subsp. *lactis, Lactobacillus helveticus, Lactobacillus delbrueckii* subsp. *bulgaricus* and *Lactobacillus acidophilus*.

In particular, lactic acid bacteria cultures (LAB-cultures) have found widely commercial use. Thus a preferred embodiment of the invention is a LAB-culture that comprises one or more organisms selected from the group comprising *Lactococcus* spp., *Streptococcus* spp., *Enterococcus* spp., *Lactobacillus* spp., *Leuconostoc* spp., *Pediococcus* spp. and *Bifidobacterium* spp.

Commercial starter cultures are frequently categorized according to their applications. An O-culture is used to make cheese without holes (Cheddar, Cheshire, Feta) and typically comprises one or more organisms selected from the group comprising *Lactococcus lactis* subsp. *lactis* and *Lactococcus lactis* subsp. *cremoris*. A D-culture is used to make butter and typically comprise one or more *Lactococcus* species i.e. *Lactococcus lactis* subsp. *lactis, Lactococcus lactis* subsp. *cremoris* and *Lactococcus lactis* subsp. *lactis* biovar *diacetylactis*. A L-culture can conveniently be used to produce cheese with only small holes (cottage cheese) and curdled milk products with low $CO_2$-production. Typically organisms in an L-culture are *Lactococcus lactis* subsp. *lactis, Lactococcus lactis* subsp. *cremoris* and *Leuconostoc* spp. And finally, a LD-culture is used to make cheese with normal hole sizes, curdled milk products (junket)) and sour butter. Commercially, a LD-culture is currently one of the most used mixed cultures. A LD-culture typically comprises one or more organisms selected from the group comprising *Lactococcus lactis* subsp. *lactis, Lactococcus lactis* subsp. *cremoris, Lactococcus lactis* subsp. *lactis* biovar *diacetylactis* and *Leuconostoc* spp.

As is the case of other types of mixed starter cultures the specific amount of the individual bacterial species in a LD-culture may vary in accordance with the specific required use. The skilled person is aware of this and capable of determining the preferred mixed culture composition according to the required needs.

For instance, if aroma is required an optimal composition of the aroma making bacteria *Lactococcus lactis* subsp. *lactis* biovar *diacetylactis* and *Leuconostoc* spp. should be preferred.

A preferred LD-culture Comprises:

TABLE 1

LD-culture composition.

| | |
|---|---|
| *Lactococcus lactis* subsp. *lactis*, | 60-95%, |
| *Lactococcus lactis* subsp. *cremoris* | preferably 70-90% |
| *Lactococcus lactis* subsp. *lactis* biovar *diacetylactis*, | 5-40%, preferably |
| *Leuconostoc* spp | 0.1 to 30% |

Within the ranges above, it is preferred to have from 0.25 to 6% of *Leuconostoc* spp and from 7 to 30% of *Lactococcus lactis* subsp. *lactis* biovar diacetylactis.

Of course the total percentage sum of the 4 different LAB specifies cannot exceed 100%. However, it may be less than 100% if other bacteria than the 4 mentioned ones are present in the LD-culture. Example 2 herein provides an example of a stabilized LD-culture.

Fungal cultures are another group of microbial starter cultures, which may be used in accordance with the invention. Fungal cultures, such as yeast cultures and cultures of filamentous fungi, are commonly used in the manufacture of certain types of cheese and beverage. Examples of currently used cultures of fungi include *Penicillium roqueforti, Penicillium candidum, Geotrichum candidum, Torula kefir, Saccharomyces kefir* and *Saccharomyces cerevisiae*.

A particular preferred embodiment of the present invention is culture-comprising *Lactobacillus acidophilus*.

In a further aspect the invention provides a method for making a frozen culture comprising following steps: 1) adding the cryoprotective agent selected from the group consisting one or more compound(s) involved in the biosynthesis of nucleic acids or one or more derivative(s) of any such compounds to a concentrated culture of viable organisms, 2) freezing the material to get frozen material, and 3) packing the frozen material in a suitable way.

It will be understood that the freezing and packing steps can be performed in a multitude of ways.

The freezing step should be optimized to ensure the cell's survival. Certain cells (e.g. most LAB) may be directly frozen, that is, brought directly into contact with an agent already at cryopreservation temperature. Direct methods include dripping, spraying, injecting or pouring cells directly into a "cryogenic temperature" fluid such as liquid nitrogen, liquid CO2, or liquid helium. In the present context cryogenic temperatures refer to temperatures below −50° C., preferentially to temperatures below −150° C. (123° K.). Cells may also be directly contacted to a chilled solid, such as a liquid nitrogen frozen steel block. The cryogenic fluid may also be poured directly onto a container of cells. The direct method also encompasses contact cells with gases, including air, at a cryogenic temperature. A cryogenic gas stream of nitrogen or helium may be blown directly over or bubbled into a cell suspension. Indirect method involved placing the cells in a container and contacting the container with a solid, liquid, or gas at cryogenic temperature. The container for the indirect freezing method does not have to be impermeable to air or liquid. For example, a plastic bag or a Tetra-Pak® are adequate.

In one preferred embodiment, the culture is concentrated, e.g. by centrifugation or ultrafiltration, the cryoprotective agent(s) is (are) added to. the culture and the culture is subsequently added drop wise into liquid $N_2$ forming frozen culture granula. The frozen culture granula is then collected and packed in order could to be provided to the user. The frozen culture granula may be packed in a bottle, a tetra-pack®, a bag, or any container which is suitable for the purpose. The frozen and packed culture granula are typically kept and distributed at temperatures which ensures that they stay frozen until they are to be used for inoculation of the media to be fermented or processed.

In yet a further aspect the invention provides a method for making a freeze dried culture comprising following steps: 1) adding a cryoprotective agent selected from the group comprising or consisting of one or more compound(s) involved in the biosynthesis of nucleic acids or one or more derivative(s) of any such compounds to viable organisms, 2) freezing the material to get frozen material, 3) sublimation of water from the frozen material, and 4) packing the freeze dried material in a suitable way. The addition of cryoprotective agent(s), the optional concentration step, the freezing (or freeze-drying) and the packing steps can be performed as described.

Whereas frozen cultures need to be shipped and stored at low temperatures freeze-dried or lyophilised cultures can be shipped and stored without refrigeration for extended periods of time, provided that they are kept at dry conditions. However even in the case of freeze-dried cultures, storage below 0° C. is recommended.

Typically both frozen and freeze-dried cultures according to the invention are provided as commercial DVS®-starter or Redi-Set® cultures. One advantage of the DVS®-starter cultures is that they may be added directly to the medium containing production fermentor or container in the form of frozen or freeze-dried cells. This results in an almost instantaneous regeneration of viable cells. Many of the, commercially distributed starter. cultures are lactic acid bacteria cultures, thus, a preferred-embodiment of the present invention is the frozen or freeze-dried lactic acid bacteria (LAB) culture obtained as described.

In a further aspect, the invention pertains to a method of preparing a food or a feed product said method comprising using a frozen of freeze-dried culture according to the invention.

In a specific embodiment the food product is a milk-based product such as cheese, yoghurt, butter or a liquid fermented milk product, such as e. g. buttermilk, Ymer, Butter or drinking yoghurt. In another embodiment of the invention, the food-product is a cheese including: soft cheese types, including but not limited to Camenbert, Brie, Argentine Port Salut, Crezenza, and Gorgonzola; Emmenthal cheese types, including but not limited to Emmenthal and Gruyere; Cottage cheese types, including but not limited to Cottage cheese; Feta cheese types, including but not limited to Feta and White cheese; Continental cheese types, including but not limited to Gouda, Edam, Maasdam, Samsoe, Saint Paulin, Raclette, Manchego, and Prato; Pasta Filata cheese types, including but not limited to Mozzarella, Pizza cheese, Provolone, and Kaskawal; Cheddar cheese types, including but not limited to Cheddar, Territorials, American Cheddar, Monterey Jack, and Colby; and Grana cheese types, including but not limited to Grana, Parmesan, and Sbrinz.

Furthermore, the food product may be selected from a meat product, a vegetable product and a beverage such as wine and beer.

Another significant application of the method according to the present invention is the use of the liquid starter cultures as so-called probiotics. By the term "probiotic" is in the present context understood a microbial culture which, when ingested in the form of viable cells by humans or animals, confers an improved health condition, e. g. by suppressing harmful micro-organisms in the gastrointestinal tract, by enhancing the immune system or by contributing to the digestion of nutrients. A typical example of such a probiotically active product is "sweet *acidophilus* milk".

In further embodiments, the method according to the invention is used in the production of an animal feed such as silage e. g. grass, cereal material, peas, alfalfa or sugar-beet leaf, where bacterial cultures are inoculated in the feed crop to be ensiled in order to obtain a preservation hereof, or in protein rich animal waste products such as slaughtering offal and fish offal, also with the aims of preserving this offal for animal feeding purposes.

The invention is further illustrated in the following non-limiting examples and the figures.

EXAMPLES

Figure 1:
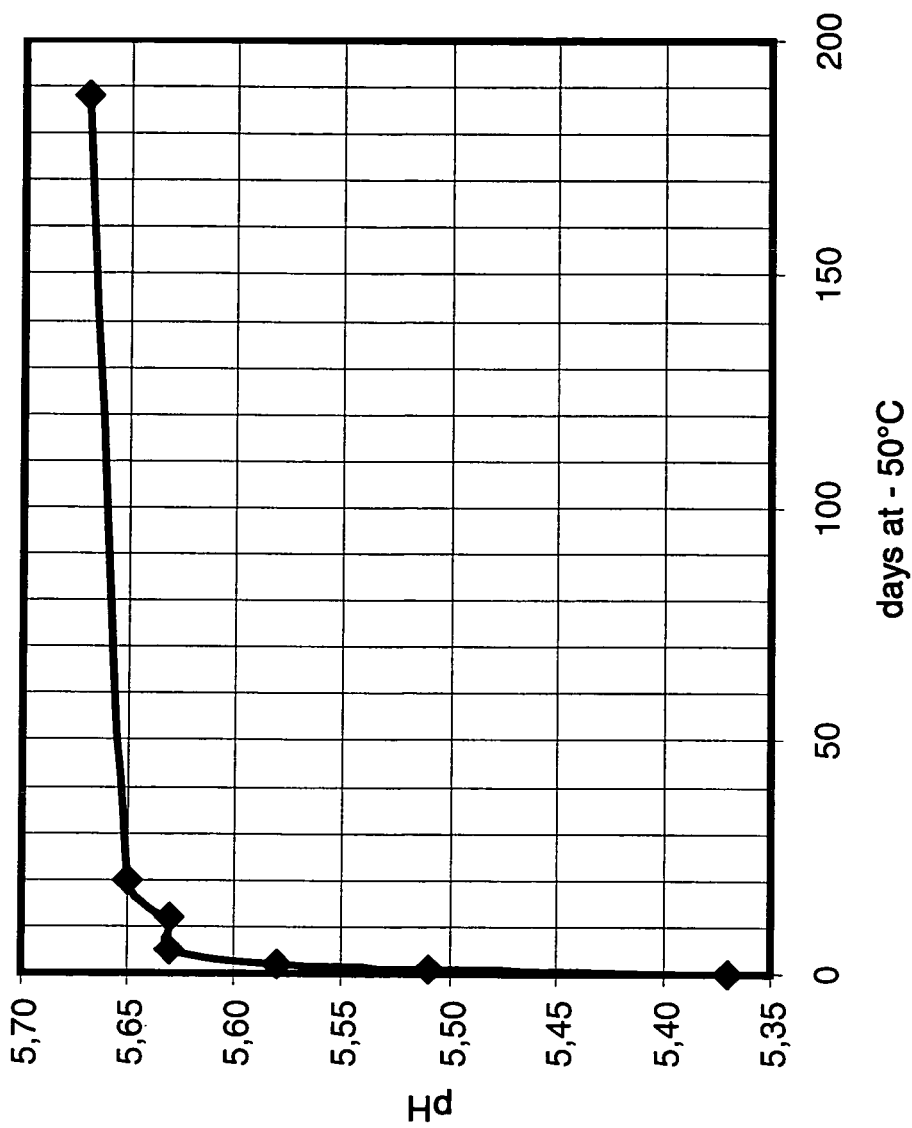
FIG. 1. Shows the stability of a commercial frozen concentrated culture (F-DVS™ Fl-Da N, Chr. Hansen A/S Item. No. 501691) during the initial phase of storage at −50° C. The activity of the culture is determined by the acidifying activity assay using an amount of inoculation material, which is 0.01% w/v. The pH was measured after 6 hrs. of incubation at 30° C. in milk. Note: a higher pH is indicative of less acidifying activity (i.e. less metabolic activity) of the culture.

Materials and Methods
Cultures:
The following commercially available cultures were used: Fl DaN, CH N 14 and CH N19. All three cultures are commercially available frozen LD-cultures in the form of Frozen Direct Vat Cultures (F-DVS™), from Chr. Hansen A/S, Denmark as: F-DVS™ Fl-Da N (Chr. Hansen A/S Item. No. 501691), F-DVS™ CH-N 14 (Chr. Hansen A/S Item. No. 200118), F-DVS™ CH-N 19 (Chr. Hansen A/S Item. No. 501593).

Fermentation Media and Fermentation Conditions:
Medium Composition for Culture of LD-cultures:
The LD-cultures-were cultured in a medium-having the following composition: Casein hydrolysate (Oxoid, Basing-stoke, UK, Product Code L41), 30 g/l; Primatone RL (Quest, Naarden, The Netherlands, Product Code 5X59051), 30 g/l; soya peptone (Oxoid, Basing-stoke, UK,. Product Code L44), 30 g/l; yeast extract (Oxoid, Basingstoke, UK, Product Code L21), 15 g/l; MgSO4, 1.5 g/l; Na-ascorbate, 3 g/l; and lactose 50 g/l.

The medium was sterilized by UHT-treatment (143° C. for 8 sec.). The finished medium had a pH of 6.5.

Fermentation Condition for LD-cultures:
The fermentation was performed in a 100 l fermentation tank at 30° C. using 1% (w/w) of the culture mentioned above as inoculum. The anaerobic fermentation was run with nitrogen in the headspace and a headspace pressure of about 0.2 bar. The cultures were allowed to acidify to pH 6.0. The pH was subsequently maintained at 6.0 by controlled addition of 13.4 N $NH_4OH$.

When no further base consumption was detected, the respective culture was cooled down to about 10° C.

Postfermentation Treatment of LD-cultures:
Following cooling, the bacteria in fermentation broths were concentrated 10-20 times by centrifugation additives added and subsequently frozen as pellets in liquid nitrogen at one atmosphere of pressure if not otherwise indicated. The acidifying activity of pellets were measured at various times after freezing the rest of the pellets were stored at −50° C. until further analysis, unless otherwise indicated.

Additives:
Additives were obtained as indicated: inosine-5'-monophosphate (IMP) (Alsiano A/S, Birkeroed, DK), adenosine-5'-monophosphate (AMP) (Sigma A2252), uranosine-5'-monophosphate (UMP) (Sigma U6375), cytidine-5'-monophosphate (CMP) (Sigma C1006), Na-formate (Kirsch Pharma, Salzgitter, DE), adenosine (Alsiano A/S, Birkeroed, DK), guanosine (Alsiano A/S, Birkeroed, DK) and inosine (Alsiano A/S, Birkeroed, DK).

Acidifying Activity Assay and CFU Analysis:
Frozen culture was inoculated on a 0.01% (w/w) level in 200 ml UHT-sterilized reconstituted skimmed milk (RSM) containing 9.5% (w/w) solid matter and heated at 99° C. for 30 minutes (LAB-milk). The RSM was incubated at 30° C. for 6 h to permit acidification of the substrate material. The acidification activity was measured as described in Example 6: Analytical Procedure QAm-052, "acidification activity—UHT", Chr. Hansen A/S (Denmark).

Simulated Cheese Production After a DANBO Temperature-profile:
The acidification is performed according to a temperature profile reflecting the temperature time-course which the culture will typically encounter when used in the dairy for production of a given dairy product in this case the DANBO cheese.

pH is measured at a fixed times as indicated in table 2.

TABLE 2

| The Danbo profile | | |
|---|---|---|
| Time, minutes | Temperature, ° C. | Variation |
| 02:40 | 31.0° C. | ±0.2° C. |
| 00:15 | Ramp 31.0° C. to 38.0° C. | ±0.5° C. |
| 00:35 | 38.0° C. | ±0.2° C. |
| 04:24 | Ramp 38.0° C. to 16.0° C.* | ±0.5° C. |
| up to 16:00 | 16.0° C. | ±0.2° C. |

The acidification activity was measured as described in example 7: Analytical Procedure QAm-043, acidification activity—"Programmed temperature profile" Chr. Hansen A/S (Denmark).

CFU analysis was measured and calculated as described in example 8: Analytical Procedure Q-AM-071, "Enumeration of microorganisms" Chr-Hansen A/S (Denmark).

Example 1

Stability Study of Frozen LD-culture of Fl-Da N

In this example the stability measured by the acidification activity of a commercially produced LD-culture: F-DVS™ FI-Da N (Chr. Hansen A/S Item. No. 501691) was followed over a period of 6 months. The culture was produced and stored at −50° C. as described in the Materials and Methods section.

In contrast to what is common the first activity-measurement in this example was performed immediately after the culture were frozen as pellets in liquid nitrogen and followed by measurements after 1, 2, 12, 20 and 188 days of storage at −50° C.

The results of this experiment are shown in FIG. 1.

The acidification activity was drastically decreased during the very first few days of storage. After only one week of storage the acidification activity was reduced with 0.26 pH unit. This reduction is equivalent to a 50% reduction of the acidification activity after only one week of storage. After two weeks of storage further loss of the cultures acidification activity became less pronounced and the acidification activity of the culture only decreased marginally during the rest of the period.

The unexpected result of this experiment made the inventors realize that there were significant and hitherto unrecognized stability problems which related to the freezing and the initial phase of the storage of some types of commercial relevant concentrated frozen lactic acid bacteria cultures, such as e.g. commercial available frozen LD-cultures.

Example 2

Stability Study of Frozen LD-culture of CH N14 Using IMP as Cryoprotective Agent This example describes the stability study with frozen direct vat set cultures (F-DVS™) of CH N14 formulated with IMP as cryoprotective agent. In the experiments the concentration of IMP was kept at 3% w/w per gram concentrated biomass. The IMP was added to the concentrate as a 30% w/w sterile solution.

After fermentation, biomass was harvested and concentrated via centrifugation from fermentation broth of F-DVS™ CH N 14. The cell concentrate was divided into two portions of 300 gram each and IMP was added to one of the portion.

The additives and concentrates were mixed for 30 minutes, frozen in liquid nitrogen and subsequently stored at −50° C. The frozen culture had a content of viable bacteria of at least $10^{10}$ colony forming units (CFU) per g frozen material. Culture activity in milk (LAB-milk) was measured following 3 days of storage at −50° C. and the activity was followed periodically up to 65 days.

Figure 2:
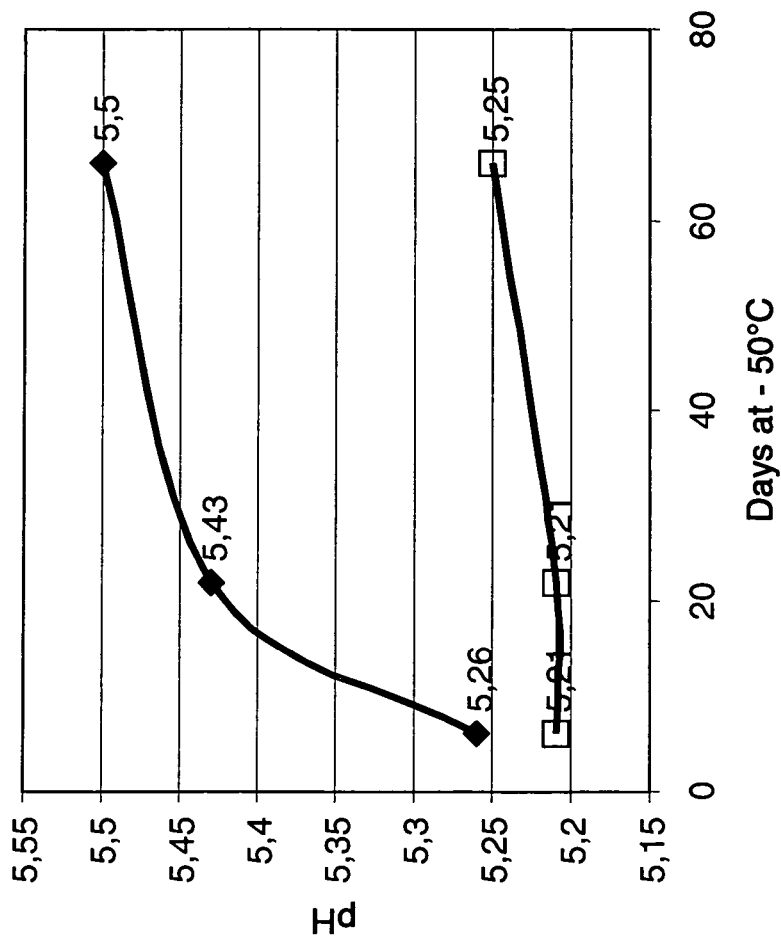
FIG. 2. Shows the storage stability expressed as the acidifying activity of frozen concentrated culture F-DVS™ CH-N 14 (Chr. Hansen A/S Item. No. 200118). with and without 3% w/w IMP added. Note: the ordinate shows the pH measured after 6 hrs. of incubation at 30° C., amount of inoculation material: 0.01% w/v. A higher pH is indicative of less acidifying activity (i.e. less metabolic activity) of the culture. Open squares indicate cultures added IMP, whereas diamonds indicate cultures without IMP.

Stability profiles for F-DVS™ of CH N14 given as acidification activity are summarized in FIG. 2.

It is evident that F-DVS™ CH N14 free of additives is loosing activity. The reduction in stability is equal to 0.25 pH units for CH N 14 after storage for 65 days at −50° C. 0.25 pH units is nearly equal to a 50% loss of acidification activity (i.e. the stabilized culture is approximately 2 times as active as the unstabilized culture).

Example 3

Stability Study of Frozen LD-culture of F-DVS™ CH N14 Using IMP as Cryoprotective Agents Tested After a Temperature Profile In this experiment samples from the culture described in Example,2 were tested after storage for approximately two months at −50° C. The acidification activity was measured at several time points during the incubation according to a simulated "Danbo" temperature profile—see table 2. The fermentation medium was low pasteurized full milk similar to the milk that normally is used for commercial production of Danbo cheese.

The acidifying activity of cultures with and without inosine-5'-monophosphate (IMP) added prior to freezing was compared.

One set of bottles with low pasteurized full milk was inoculated with a frozen CH N14 culture without added IMP. In this case the amount of culture added was 0.01%, 0.02% and 0.03%, respectively (w/w%).

Another set of bottles with low pasteurized full milk was inoculated with a frozen CH N14 culture with 3% (w/w%) IMP added prior to freezing. In this case the amount of culture added was 0.01% (w/w%).

As seen in example 2 the culture without IMP. lost approximately 50% of the acidification activity which is equivalent to that a culture with IMP added has an activity that is nearly twice the activity compared to a similar amount of a similar culture without added IMP.

To illustrate the booster effect of IMP the sample without IMP added was inoculated using three different amounts of CH N14 culture. Judged from the results obtained in example 1 (i.e. that a little less than 50% of the activity is lost during storage of a culture without IMP added) one would expect that the acidification activity of a 0.01% inoculum of a. culture with IMP added would be somewhere between the acidification activity of a 0.01% and a 0.02% inoculum of a culture without IMP added.

Figure 3:
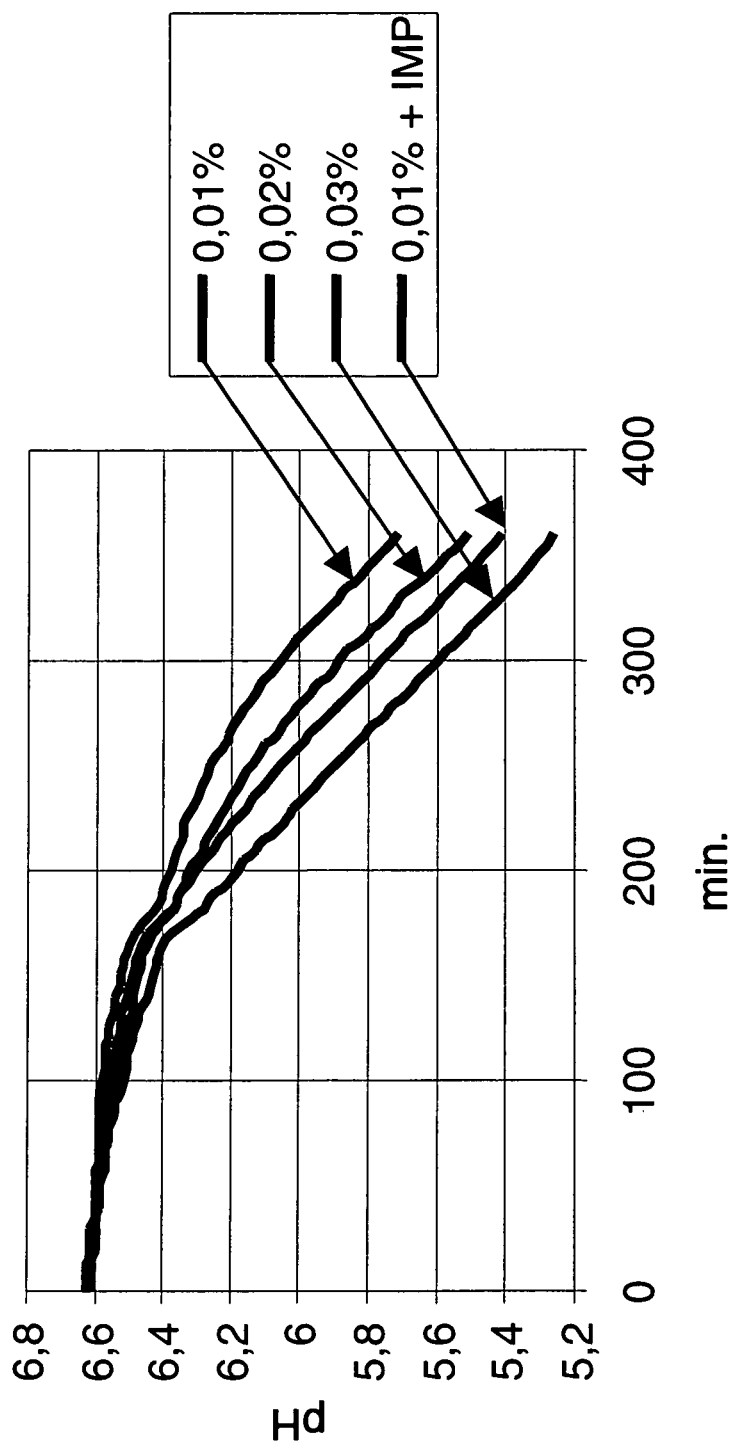
FIG. 3. Shows the acidifying activity of F-DVS™ CH-N 14 cultures (Chr. Hansen A/S Item. No. 200118) with and without IMP added. The fermentation was performed with cultures after 2 months of storage at −50° C. The fermentation was tested in low-pasteurized full milk following the Danbo temperature-profile of Table 2. The amounts of culture added are given in % (w/v). Note: the ordinate shows the pH measured after 6 hrs. of incubation at 30° C. A higher pH is indicative of less acidifying activity (i.e. less metabolic activity) of the culture.

However, as illustrated in FIG. 3, this is not the case. The acidification activity of a 0.01% inoculum of a culture with IMP added turned out to be somewhere between. the acidification activity of a 0.02% and a 0.03% inoculum of a culture without IMP added. This extra activity we ascribe to the booster effect of the added IMP.

This experiment shows that addition of IMP to a culture results in a 2-2.5× higher activity compared. with the addition of a similar amount of a similar culture without IMP added.

The booster effect was not apparent in example 2, because in example 2 the milk had been subjected to a rather harsh heat sterilization procedure, i.e. LAB milk. In our experience, the booster effect is most pronounced in milk used for cheese fabrication since such milk typically is low-pasteurized milk.

Example 4

Loss of Activity During Freezing of CH-N 19

This example describes the loss of activity during the freezing of a CH N19 culture formulated with IMP as cryoprotective agent. In the experiments the concentration of IMP was kept at 3% w/w per gram concentrated biomass (added as a sterile 30% w/w solution).

After fermentation, biomass was harvested and concentrated via centrifugation from the fermentation broth of the CH-N 19 culture. The cell concentrate was divided into two portions of 300 gram and IMP was added to one of the portions. The additives and concentrates were mixed for 30 minutes and subsequently 150 g of the two portions was frozen in liquid nitrogen. The culture had a content of viable bacteria of at least $10^{10}$ colony forming units (CFU) per g frozen material. Frozen and non-frozen cultures with and without added IMP were tested for their acidifying activities immediately after they were produced. Culture activity in milk (heat sterilized LAB-milk) was measured.

Figure 4:
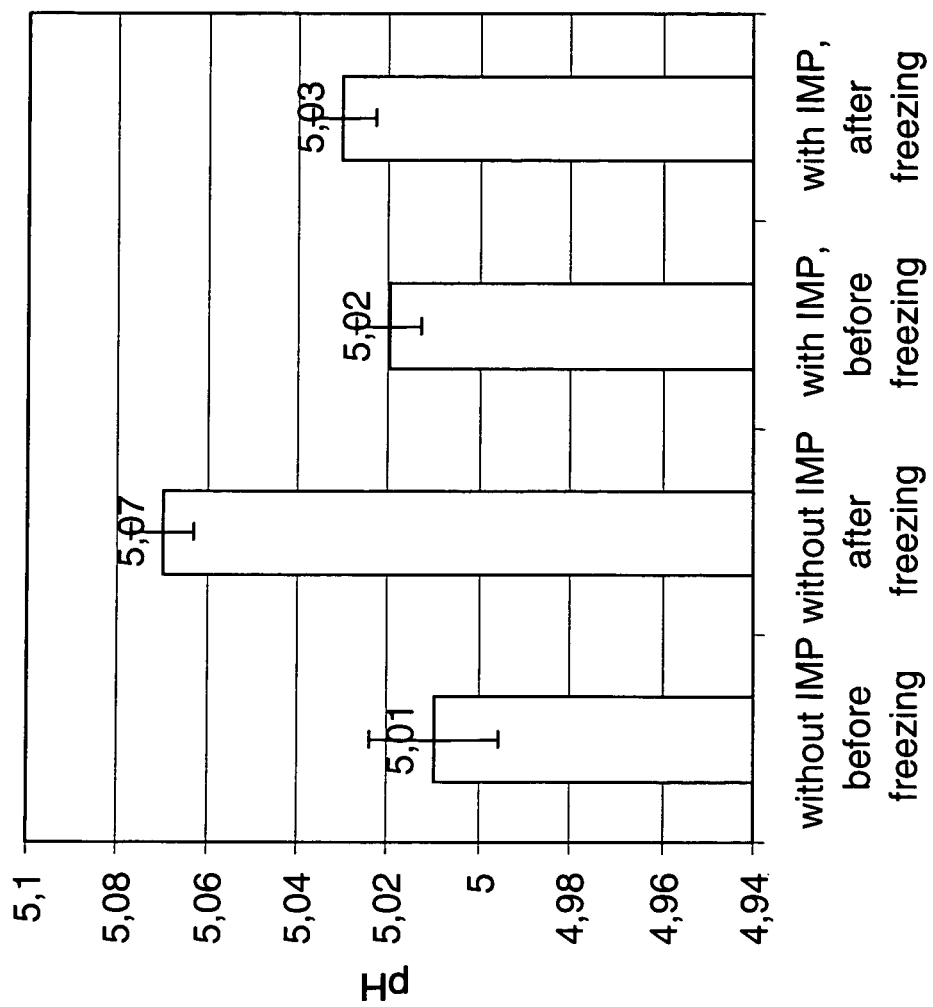
FIG. 4. Illustrates loss of activity during freezing of the F-DVS™ CH-N 19 culture (Chr. Hansen A/S Item. No. 501593). The culture was tested for activity same as the culture was produced (on day 0). Error bars indicate the standard deviation. Note: the ordinate shows the pH measured after 6 hrs. of incubation at 30° C., amount of inoculation material: 0.01% w/v. A higher pH is indicative of less acidifying activity (i.e. less metabolic activity) of the culture.

The results shown in FIG. 4 show a loss of acidifying activity of 0.06 pH units if the culture was frozen without added IMP. A loss of 0.06 pH units is equivalent to a 5-10% loss of acidifying activity. However if IMP was added to this culture no significant loss of activity was observed. The difference of 0.01 pH units is of same size as the standard error as indicated by the error bars on the figure.

It is concluded that IMP also is able to act as a cryoprotective agent and counteract the impact exerted by the freezing of this type of culture.

Example 5

Dose Response for IMP Using Culture of F-DVS™ Fl-Da N

This example describes the dose response study with frozen cultures (F-DVS™) of Fl-Da-N formulated with IMP as cryoprotective agent. In the experiments the concentration of IMP were 0%, 0.1%, 0.5%, 1%, 3% and 6% w/w per gram concentrated biomass. The additive was added to the concentrate as a 30% sterile solution.

After fermentation, biomass was harvested and concentrated via centrifugation from fermentation broth of Fl-Da N. The cell concentrate was divided into 6 portions of 300 gram and IMP was added to each one of the portions. To simulate a situation similar to the industrial situation during the freezing process the additives and concentrates were mixed and stored for 5 hours at 8° C. and subsequently frozen in liquid nitrogen and further stored at −50° C. Thus this example cannot be compared with the previous examples. The frozen culture had a content of viable bacteria of at least $10^{10}$ colony forming units (CFU) per g frozen material. Culture activity in milk (LAB-milk) was measured the same day as the frozen cultures were formulated.

Figure 5:
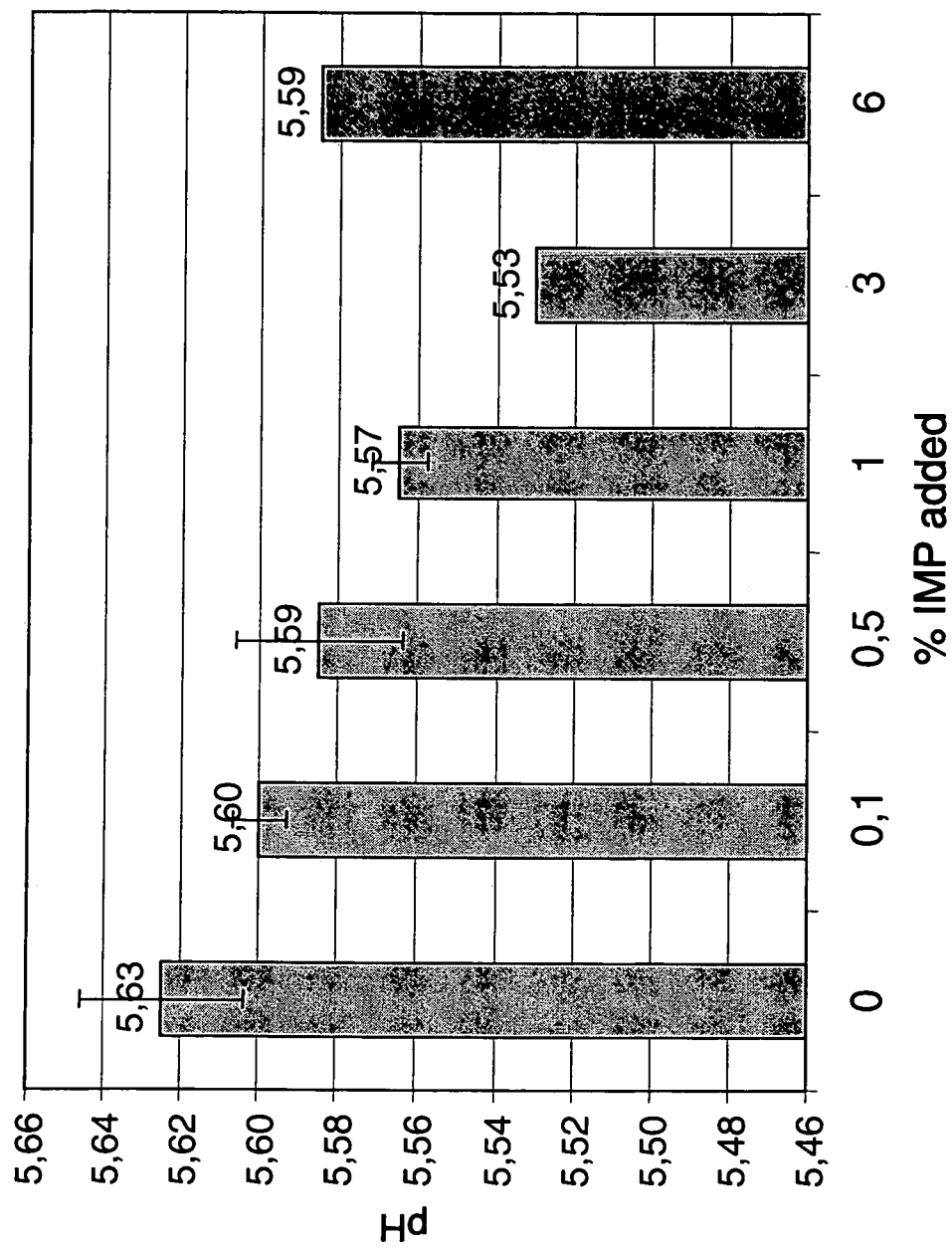
FIG. 5. Illustrates the loss of acidifying activity of a F-DVS™ Fl-Da N culture (Chr. Hansen A/S Item. No. 501691) as a function of the amount of IMP added. Concentrates were stored as liquid at 8° C. for 5 h before. freezing. Error bars indicate the standard deviation. Note: the ordinate shows the pH measured after 6 hrs. of incubation at 30° C., amount of inoculation material: 0.01% w/v. A higher pH is indicative of less acidifying activity (i.e. less metabolic activity) of the culture.

Results are shown in FIG. 5.

From these results it is clear that the concentrated cultures, which were frozen without, added IMP showed the largest loss. of acidifying activity. The optimal result (i.e. smallest decrease of acidifying activity) was obtained with addition of 3% (w/w%) IMP.

Example 6

Analytical Procedure QAm-052, "Acidification Activity—UHT", Chr. Hansen A/S (Denmark)

Application

This method is used for determination of acidification activity.

Principle

For F-DVS™ and FD-DVS products:

The culture is diluted and inoculated into milk. Incubate over a given time at a given temperature. After incubation pH is measured.

For Frozen Redi-Set® (F-RS) and Freeze-dried Redi-Set® FD-RS products:

For these products, the activity analysis consists of 2 growth steps. A bulk starter is prepared by growing the culture in milk over a given time and temperature. After this the bulk starter is inoculated in milk, and after a new incubation pH is measured.

Analysing Parameters

Statement of the products analysing parameters can be read in Laboratory Information Management System (LIMS). Examples: Type of milk, Temperature of milk at 1st and 2nd weighing, Incubation time, Incubation temperature, Inoculation percent for the samples and control standards.

Apparatus and Reagents pH-meter; pH electrode; Calibration buffers, pH 7.00±0.01 and pH 4.01±0.01; Water bath with a thermostate, precision ±0.2° C.; Temperature sensor; Balance, precision 0.01 g with minimum two decimals; Rotation apparatus; Thermometer; Watch; Magnetic stirrer; Magnets; Beakers, 50 ml.

Procedure

Preparation of analysis:

Note: All flasks should originate from the same batch i.e. with the same date.

At least 16 hours before start of analysis the lids on all bottles are loosened. Water bath/s is/are tempered to incubation temperature. Bottles for 1st weighing are tempered to inoculation temperature (can be either cold or hot milk). Buffer pH 4.01 and pH 7.00 are placed in water bath at incubation temperature at least 30 min before calibration of pH meter.

Note: For samples, which are placed in ice bath at 4° C. before incubation, the heating of the water bath is started by a timer.

Preparation of Samples Before Analysis

Frozen cultures: Frozen samples/control standards are before 1st weighing placed in a foam box with dry ice and are kept here till all weighings are done.

Frozen cultures, which are thawn before use:

For frozen products, where a whole carton is used, the product is thawn according to, see local instruction. After thawing the sample may be kept at 4° C. for max. 30 min, before use. For frozen cultures in cans, a can is placed in a water bath at 22° C. for 20 min in order to thaw the contents. After thawing the culture may be kept at 4° C. for max. 30 min. before use.

Freeze dried cultures:

Freeze dried samples/control standards are acclimatized at room temperature for at least 15 min before start of analysis.

Inoculation Procedure

1st weighing/dilution:

The bottle for the 1st weighing is placed on the balance, which is set to zero.

Weighing of Product/control Standards is Carried out Directly into the Milk

Time for 1st weighing is always entered when inoculation is carried out in warm milk. The actual amount of inoculum (1st weighing) is entered with at least two decimals.

Frozen and thawn products are shaken carefully until the product has been distributed or max. 10 times, after which the bottle stands for approx 50 sec.

For freeze dried products the rotation apparatus (speed 2) is used for 5 min or until the products has been distributed.

Note: For freeze dried products of L. acidophilus, Bifidobacterium or L. casei, all inoculations are carried out in a clean bench.

2nd Weighing

The bottle for the 2nd weighing is placed on the balance, which is set to zero.

For frozen and thawn products, the dilution bottle is shaken carefully before 2nd weighing is carried out. The $2^{nd}$ weighing is carried out according to current quality control (Qc) procedures at time 1 minute.

For freeze-dried products the 2nd weighing is carried out according to current Qc.

Time for 2nd weighing is entered when the inoculation are cold/warm. The actual amount of inoculum (2nd weighing) is entered with at least 2 decimals.

The activity bottle is turned and the inoculation procedure is repeated for next samples/control.

Activity bottles, which are inoculated from the same 1st weighing, are inoculated in succession.

Note: Weighing off mixed products:

At first one 1st weighing is prepared from each control standard/single strain. From each of these the 2nd weighings are carried out to the same activity bottle, so this will contain all control standards/single strains.

For frozen products the time from the first weighing to the last 2nd weighing must be max. 5 min. For freezedried products the time from the first 1st weighing to the last 2. weighing must be max. 10 min.

At last place a uninolulated bottle of milk in the waterbath.

For products where 1st weighing takes place in cold milk:

$$\text{Time}_{(measurement)} = \text{Time}_{2.\ weighing} + \text{Time}_{incubation}$$

or products where 1st weighing takes place in hot milk:

$$\text{Time}_{(measurement)} = \text{Time}_{1st\ weighing} + \text{Time}_{incubation}$$

Note: For products, which in addition are analysed for a long time acidification, the inoculation for this can be carried out at the same time as the inoculation for acidification activity.

From 1st weighing used for acidification activity, 2nd weighing can be done in cold activity milk, which is placed at 4° C. until incubation in a water bath, which is heated to incubation temperature. In this case the bottles are incubated for ½ hour more than the given incubation time.

Note: For products where both inoculation and pH measurement of samples/Control standards, due to a long acidification time, is impossible within normal working hours, the 1st and 2nd weighing can be carried out in cold milk.

After inoculation of the activity milk, the bottles are placed in a water bath with cooling. The temperature sensor from a contact watch is placed in a bottle with uninoculated milk, which is placed in the water bath. A contact watch is connected to start heating of the water at a given time, and first when the temperature for the product of concern the incubation time starts.

Note: If it is necessary to use more than one water bath the Control standard MUST be incubated together with its connected samples in the same water bath.

Measurement of pH Electrode

Calibration is carried out according to current instructions regarding electrode calibration and maintenance.

Measurement of pH Meter pH must be measured in the samples/Control standards at $\text{Time}_{measurement}$. If time exceeded more than one minute, it is notes. If time is exceeded more than two minutes, the measuring is skipped. Just before time of measurement the bottle is turned 180°.

The pH measurement is carried out in the bottle or in a sample, which is poured in a 50 ml beaker with magnet stirring.

pH is entered with at least 2 decimals.

Possible remarks on the measurement are entered. The measuring procedure is continued till all samples/control standards and the uninoculated milk are measured. The temperature of the water bath is measured in an inoculated bottle of milk and entered in the logbook.

Finally, pH in calibration buffers is measured.

Example 7

Analytical Procedure QAm-043, Acidification Activity—"Programmed Temperature Profile" Chr. Hansen A/S (Denmark).

Application

This method is used for determination of acidification activity according to Pearce test and in other situations where acidification is performed according to a temperature profile e.g. Danbo-profile. Only Pearce test is included by the IDF standard.(*international dairy standard*)

Principle

The acidification is performed according to a temperature profile reflecting the temperature course, which the culture will typically encounter when used in the dairy for production of a given dairy product.

For Pearce test this is the cheese making temperature during the production of Cheddar.

pH is measured at a fixed time.

For cultures where rennet is not added during analysis, a continuous pH measurement may be applied.

Analysing Paramters

Analysing parameters, which are product specific, are given in LIMS.

Definition of temperature profile (for products where Pearce profile is not used).

Control standard to be used.

Type of pH measurement.

Inoculation percents for sample and control standards.

Dilution milk: 206.9 g cold (4° C.) LAB-milk (i.e. UHT-sterilized reconstituted skimmed milk (RSM) containing 9.5% (w/w) solid matter and heated at 99° C. for 30 minutes).

Activity milk: 200 g cold (4° C.) low pasteurised whole milk 3.5% fat.

Rennet: Naturén® standard 190 diluted 1:40 with water.

Apparatus and Reagents pH meter/pH meter for semi continuously pH measurement eks. Radiometer® PHM92.

pH electrode Radiometer® PFC2401.

Buffers: pH 7.00±0.01 and pH 4.01±0.01.

Water bath with a thermostat programmed for heating according to a predetermined temperature profile ±0.2° C.

Temperature sensor.
Balance, precision 0.01 g with minimum two decimals
Watch.
Magnetic stirrer.
Magnets
Beakers, 50 ml.
Small plastic cups.
Rotation apparatus.
Procedure
 Preparation of Analyze
 All bottles should be from the same batch i.e. with the same date.
 Water bath/s is/are tempered to the initial temperature of the temperature profile to be used.
 Bottles for dilution (=1st weighing) and for activity (2nd weighing) are placed at 4° C. until just befure use.
 Buffers pH 4.01 and pH 7.00 are placed in water bath at the specified measuring temperature ±0.2° C. at least 30 min before calibration of pH meter.
 Preparation of samples before analysis.
 Frozen cultures:
 Frozen samples/control standards are before 1st weighing placed in a foam box with dry ice and are kept here till all weighings are done.
 Frozen cultures, which are thawn before use:
 For frozen products, where a whole carton is used, the product is thawn according to current instructions.
 After thawing the sample may be kept at 4° C. for max. 30 min. before use.
 Freeze dried cultures:
 Freeze dried samples and control standards are acclimatized at room temperature for at least 15 min before start of analysis.
 Provided that the sample are going to be used for retest the day after, it may be stored at +8° C.
 Inoculation Procedure
 Weighing of product/control standard is carried out directly into the milk.
 The actual amount of inoculum (1st weighing) is entered with at least two decimals.
 Frozen and thawn products are turned carefully about 4 times, after which the bottle stands for approx. 50 sec.
 For freeze dried products the rotation apparatus must be used. It has to be driven with frequent speed for 5 minutes or till the product is completely soluted. This is controlled by leaving the bottle on the table for a moment and then checking the solution by looking in the bottom of the bottle.
 Note:
 If convenient for the working routine a cold, 1st weighing can stand at room temperature for max. 15 minutes before 2nd weighing.
 2nd weighing:
 The dilution bottle is turned before 2nd weighing is carried out.
 The actual amount of inoculum (2nd weighing) is entered with at least 2 decimals.
 The activity bottle is turned and the inoculation procedure is repeated for samples/control standards.
 Activity bottles, which are inoculated from the same 1st weighing, are inoculated in succession.
 2 ml rennet is added each bottle either before or after 2nd weighing. After this the bottles are turned so the rennet been distributed.
 Rennet is not added to Danbo-profile.
 (Not IDF Standard)
 The bottles are subsequently incubated at one time, as described in 6.
 In the end 2 uninoculated milk bottles are placed in a water bath. One for measuring of the water bath temperature and one for measuring pH in the blind milk.
Incubation
 Note: When more water baths are required, the control standard with corresponding samples MUST be incubated in the same water bath.
 All activity bottles are incubated at the same time in a pre-heated water bath at the defined starting temperature for the temperature profile.
 The temperature profile is started at the same time as the bottles are placed in the water bath.
 Hereafter the incubation temperature is controlled by a thermostat programmed to follow a certain temperature profile. For Pearce test see table 3 and Danbo table 4.
 The water level in the water bath should be min. 2 cm higher than the milk level.

TABLE 3

Temperature programme in Pearce profile (following the IDF)

| Time, minutes | Temperature, ° C. | Variation |
|---|---|---|
| 0 | 31.0 | ±0.2° C. |
| 50 | 31.0 | ±0.2° C. |
| 54 | 31.7 | ±0.5° C. |
| 58 | 32.2 | ±0.5° C. |
| 62 | 32.8 | ±0.5° C. |
| 66 | 33.3 | ±0.5° C. |
| 70 | 33.9 | ±0.5° C. |
| 73 | 34.4 | ±0.5° C. |
| 76 | 35.0 | ±0.5° C. |
| 79 | 35.6 | ±0.5° C. |
| 82 | 36.1 | ±0.5° C. |
| 85 | 36.7 | ±0.5° C. |
| 87.5 | 37.2 | ±0.5° C. |
| 90 | 37.8 | ±0.2° C. |
| 360 | 37.8 | ±0.2° C. |

TABLE 4

The Danbo-profile

| Time, minutes | Temperature, ° C. | Variation |
|---|---|---|
| 02:40 | 31.0° C. | ±0.2° C. |
| 00:15 | Ramp 31.0° C. to 38.0° C. | ±0.5° C. |
| 00:35 | 38.0° C. | ±0.2° C. |
| 04:24 | Ramp 38.0° C. to 16.0° C.* | ±0.5° C. |
| up to 16:00 | 16.0° C. | ±0.2° C. |

NOTE: On time 3 hours and 30 minutes, turn on the cooling water
*Manually pH measurement after 06:00 hours +/− 2 minutes correspond to a temperature in the water bath of 25.5° C. +/− 0.5° C.

CALIBRATION OF pH ELECTRODE

Calibration is carried out at initial temperature according to current instructions regarding electrode calibration and maintenance.

Measurement pH

After incubation the bottles are shaken well and pH is measured.
 The pH measurement is carried out in the bottle or in a sample, which is poured into a 50 ml beaker with magnet stirring.
 pH is entered with at least 2 decimals.
 Possible remarks on the measurement are entered.
 The measuring procedure is continued till all samples/control standards and the uninoculated milk are measured.

Finally pH in buffers are measured and entered.

Continuous pH Measurement

The pH values are sampled from the moment the temperature profile is started. After the incubation is completed, the measured pH values in both buffers at initial temperature are registered.

Example 8

Analytical Procedure Q-AM-071, "Enumeration of Microorganisms" Chr-Hansen A/S (Denmark)

Area of Application

This method is used for enumeration of lactic acid bacteria in various starter cultures and for counting of cross contaminants. The method is applicable only together with the concerned culture's analytical programme according to current quality control (Qc) procedures, why reference must be given to the analytical parameters herein.

Principle

The method is a quantitative method where the result is reported as CFU/g.

A known amount of sample is homogenized with diluent and decimal dilutions are prepared. Appropriate dilutions are mixed with Leesment Agar or spread on the surface. After incubation all colonies are counted.

Sampling

Take samples according to established microbiological principles, so that the sample is as representative as possible of the product to be examined.

Apparatus and Glassware

Bottles of 250 ml
Tubes of 20 ml with Caps
Autoclave, Operating at ±1° C.
pH-meter Sensitive to ±0.2
Balance, Operating at ±0.01 g
Whirlmixer
Stomacher
Sterile Stomacher Bags, 400 ml
Incubator, Operating ±1° C.
Water Bath, Operating ±1+ C.
Sterile Pipettes
Petri Dishes, 9 cm.
Sterile Drigalski Spatulas Media

TABLE 5

| Diluent, Contents | |
|---|---|
| Casein peptone | 15.0 g |
| NaCl | 9.0 g |
| Antifoam FG-10.2% | 1.14 ml |

Preparation

Suspend the ingredients in 1000 ml of distilled water. Heat to boiling point under frequent agitation. Dispense the diluent into bottles or tubes and autoclave at 121° C. for 15 minutes.

pH after autoclaving: 7.0±0.2.
Contents in bottles after autoclaving: 99.0±1.0 ml.
Contents in tubes after autoclaving: 9.00±0.05 ml.
If the diluent (Table 5) is to be used immediately then cool to 20° C. or lower.

Storage

The prepared diluent (Table 5) may be stored for 6 months at 5° C. in a dark place.

TABLE 6

| Leesment Agar, Contents | |
|---|---|
| Tryptone (Oxoid L42) | 20.0 g |
| Yeast extract (Oxoid L21) | 5.0 g |
| Gelatine | 2.5 g |
| Lactose | 10.0 g |
| NaCl | 4.0 g |
| Tri-sodium-citrate, 2H2O (Merck 6432) | 2.0 g |
| Calcium lactate, 5H2O (Merck 2102) | 8.0 g |
| Agar (So-Bi-Gel) | 12.0 g |

Preparation

Suspend the ingredients in 1000 ml of distilled water. Heat to boiling point under frequent agitation till complete solution. Distribute the medium into bottles and autoclave at 121° C. for 15 min. pH after autoclaving: 6.8±0.2.

If the medium is to be used inmmediately, cool it to approx. 47° C. in a water bath. Before use 2 ml 50% glucose solution has to bee added to 200 ml of Leesment Agar (Table 6) for all CR-cultures.

Is the medium used for spread plating pour 12-15 ml of melted medium into Petri dishes and let the medium set and dry for 30 min in a Clean Bench.

Glucose Solution 2.0 glucose is thawed in 100 ml. distilled water. The solution is then sterile filtered by use of a 0.20 nM filter.

Leesment-Glucose Agar

Immediately before use 2 ml. of 50% glucose solution is added to a 200 ml. Element Agar (Table 6).

Storage

The prepared Leesment Agar (Table 6) may be stored dark for 6 months at 5° C.

Poured plates packed in plastic bags may be stored dark for 10 days at 5° C.

Procedure

NB—The analytical period from weighing out the sample until the sample is pour plated or spread plated must not exceed 30 min.

Before beginning the microbiological examination, melt the medium in a boiling water bath or by boiling in an autoclave, and then cool it to 47±1° C. in a water bath.

Note—if prepoured plates are to be used the surface of the medium must be dry before plating.

In the Analytical Programme or Qc of the concerned product the following are given:

a) The amount of grammes (X) to be used for the first dilution (D1)
b) Minutes in Stomacher (M)
c) The appropriate dilutions (D2)
d) Amount to be seeded (A ml)
e) The incubation parameters
f) Plating method Preparation of Dilutions Weigh X grammes of product into a sterile Stomacher bag arid add by weighing the sufficient amount of sterile diluent to make the first dilution (D1). Place the bag in the Stomacher and treat for (M) minutes. If convenient, pour the contents of the bag into an empty, sterile bottle. By use of a sterile pipette transfer 0.1 or 1.0 ml from the lowest dilution into a bottie or tube with sterile diluent to make the next dilution (which now is the lowest!).

The contents in the bottle are mixed by shaking the bottle for 7 sec 20-25 times in an angle of 30°. The contents in the tube are mixed on a whirlmixer at maximum speed for 3×1 sec.

Allow the foam to settle and repeat point 4 and 5 until the appropriate dilution/s (D2) is/are reached.

Pour Plate

By use of a sterile pipette transfer A ml of the appropriate dilution/s (D2) into Petri dishes. Pour 10-12 ml of melted medium at not more than 47±1° C., into each Petri dish and mix well with the sample. Pour 10-12 ml of melted medium into an empty Petri dish as a control of sterility. Leave the dishes on a clean horizontal surface until the medium has set. Invert the dishes and incubate according to the concerned products Qc.

Spread Plate

By use of a sterile pipette transfer A ml of the appropriate dilution/s (D2) on to the surface of the medium. Spread the sample all over the medium by use of a sterile Drigalski spatula. Use an uninoculated Petri dish with medium as a control of sterility. Let the sample be absorbed by the medium before the dishes are inverted and incubated according to the concerned products Qc.

Counting of Colonies

For total viable cell counts Petri dishes containing between 30-300 colonies are chosen. All colonies are counted.

For counting of cross contaminants Petri dishes not containing more than 300 colonies are chosen. All colonies are counted.

Note—By counting of cross contaminants the product to be analysed may produce pinpoint colonies, which will make a cloud in the background. Therefore only colonies bigger than the pin point colonies in the cloud are counted.

Calculation

After counting a $\chi^2$-test must be carried out on the plate counts according to standard statistical procedures.

Note—The $\chi^2$-test is not carried out when the method is used for cross contaminants.

If the $\chi^2$-test is not accepted the results must be rejected and the analysis repeated.

If the $\chi^2$-test is accepted the mean number (N) of CFU/g is calculated according to below:

$$N=(\Sigma c)/((n1+0.1 n2)d)$$

where:

$\Sigma c$ is the sum of colonies counted on all Petri dishes;

n1 is the number of Petri dishes in the first dilution;

n2 is the number of Petri dishes in the second dilution;

d is the dilution factor corresponding to the first dilution.

Reporting of Results

The calculated count may be reported as in the example above or as a rounded number with two. significant digits.

Results, which are reported externally, should always be rounded.

Example 19 184 is rounded to 19 000 and is reported as $1.9 \times 10^4$.

$294 \times 10^8$ is rounded to $290 \times 10^8$ and is reported as $2.9 \times 10^{10}$.

For a three-digit number, round the third digit to the nearest zero: —If the third digit is 5 and the preceding digit is an even number, round the number down. If the preceding digit is an odd number round the number up.

Example 28 500 is rounded to 28 000 and 11 500 rounded to 12 000

Example 9

Stability Study of a Freeze-dried LD-culture of Fl-Da N

In this example, a comparison is made between the degree of alteration during the manufacturing of freeze-dried cultures (FD-DVS) of Fl-Da-N formulated with and without IMP as cryoprotective agent. In the experiments the concentration of IMP was 0% and 3% w/w per gram concentrated biomass. The additive was added to the concentrate as a 30% sterile solution.

After fermentation, biomass was harvested and concentrated via centrifugation from fermentation broth of Fl-Da N. The cell concentrate was. divided into 2 portions of 300 gram and IMP was added to one of the portions. To simulate the situation encountered in the industrial situation during a freezing process, the additives and concentrates were mixed and stored for 5 hours at 8° C. and subsequently frozen in liquid nitrogen and further stored at −50° C. for one day before freeze-drying. After freeze-drying was completed the culture was stored at −50° C. until analysis. The frozen culture had a content of viable bacteria of at least $10^{10}$ colony forming units (CFU) per g frozen material. Culture activity in milk (LAB-rnilk) was measured after 7 days of storage at −50° C.

Figure 6:
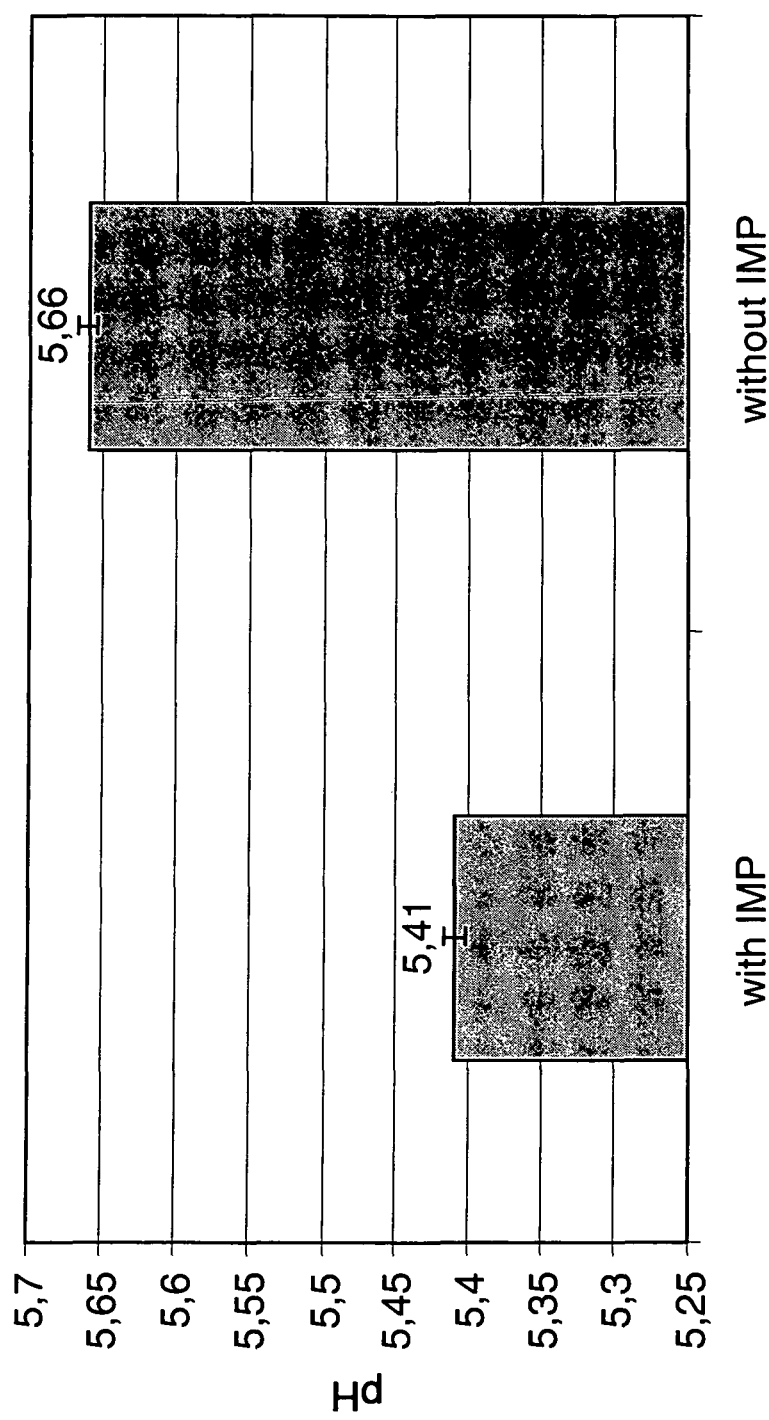
FIG. 6. Shows the storage stability expressed as the acidifying activity of freeze-dried concentrated culture DVS™ Fl-Da N culture with and without 3% w/w IMP added. The culture was tested for activity after 7 days storage at −50° C. Error bars indicate the standard deviation. Note: the ordinate shows the pH measured after 6 hrs. of incubation at 30° C., amount of inoculation material: 0.01% w/v. A higher pH is indicative of less acidifying activity (i.e. less metabolic activity) of the culture.

Results are shown in FIG. 6.

It is evident that freeze-dried DVS Fl-Dn N without added IMP has lost more activity. The reduction in stability is equal to 0.25 pH units for Fl-Dn N after storage for 7 days at −50° C. 0.25 pH units is nearly equal to a 50% loss of acidification activity.

Example 10

Stability Study of Frozen LD-culture of F-DVS™ Fl-Da N Using Different Compounds Involved in the Biosynthesis of Nucleic Acids as Cryoprotective Agents This example describes the stability study with frozen direct vat set cultures F-DVS™ Fl-Da N (Chr. Hansen A/S Item. No. 501691) formulated with either nucleotides IMP or GMP (guanosine-5'-monophosphate) or a nucleoside, Inosine as cryoprotective agent. In the experiments the concentration of IMP, GMP or Inosine was kept at 3% w/w per gram concentrated biomass. The IMP and GMP were added to the concentrate as a 25% w/w sterile aqueous solution, whereas the Inosine was added as dry powder. In the case of Inosine water was added to the culture in an amount, which equals the amount added in the case of IMP or GMP addition.

After fermentation, biomass was harvested and concentrated via centrifugation from fermentation broth of F-DVS™ Fl-Da N. The cell concentrate was divided into four portions of 300 gram each and IMP, GMP, inosine or nothing was added to one of the portions. The additives and concentrates were mixed for 30 mninutes, frozen in liquid nitrogen and subsequently stored at −50° C. The frozen culture had a content of viable bacteria of at least $10^{10}$ colony forming units (CFU) per g frozen material. Culture activity in milk (LAB-milk) was measured the same day as the cultures were frozen and the activity was followed periodically up to 13 days.

Figure 7:
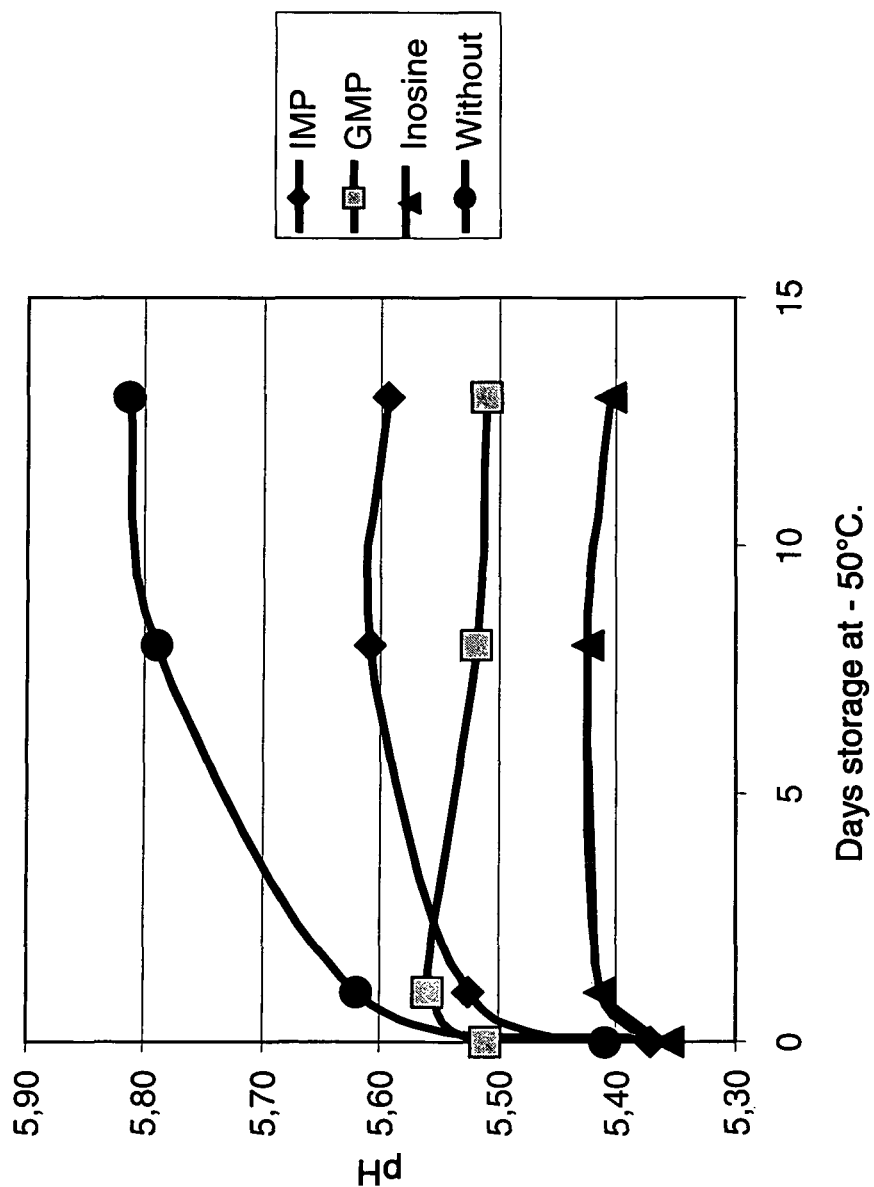
FIG. 7. Shows the storage stability expressed as the acidifying activity of frozen concentrated culture (F-DVS™ Fl-Da N, Chr. Hansen A/S Item. No. 501691) during the initial phase of storage with or without 3% w/w IMP, GMP, Inosine or nothing added. Note: the ordinate shows the pH measured after 6 hrs. of incubation at 30° C., amount of inoculation material: 0.01% w/v. A higher pH is indicative of less acidifying activity (i.e. less metabolic activity) of the culture. Solid diamond indicates addition of 3% w/w IMP, grey square indicates addition of 3% w/w GMP, solid triangle indicates addition of 3% w/w Inosine and a sphere indicates that no cryoprotective additive were added.

Stability profiles for F-DVS™ Fl-Da N given as acidification activity are summarized in FIG. 7.

It is evident that F-DVS™ Fl-Da N free of additives is loosing activity. Relative to the culture stabilized by Inosine the reduction in stability of a culture without added Inosine is equal to 0.41 pH units for F-DVS™ Fl-Da N after storage for 13 days at −50° C. 0.41 pH units corresponds to a 60% loss of acidification activity. Similarly the difference in stability between a F-DVS™ Fl-Da N culture with or without added GMP equals 0,31 pH units, which corresponds to a 50% loss of acidification activity.

Example 11

Prolonged Stability Study of Frozen LD-culture of F-DVS™ FI-Da N Using Different Compounds Involved in the Biosynthesis of Nucleic A-cids as Cryoprotective Agents.

This example describes the prolonged stability study with frozen direct vat set cultures F-DVS™ FI-Da N (Chr. Hansen A/S Item. No. 501691) formulated with either nucleotides IMP or GMP (guanosine-5'-monophosphate) or a nucleoside, Inosine as cryoprotective agents. Experimental details were as described in Example 10, with the exception that the activity was monitored for an extended period of time.

Figure 8:
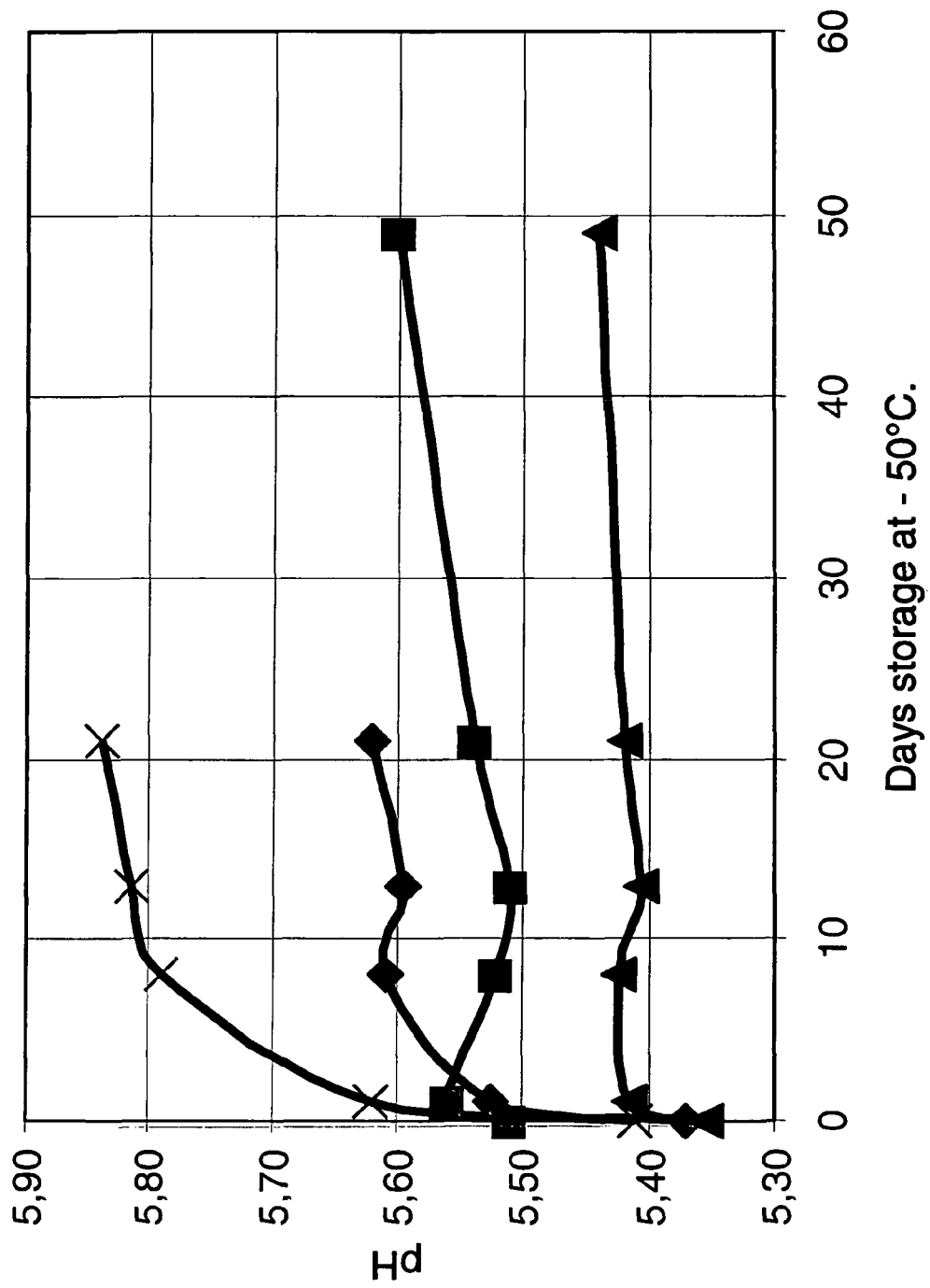
FIG. 8. Shows the storage stability expressed as the acidifying activity of frozen concentrated culture (F-DVS™ Fl-Da N, Chr. Hansen A/S Item. No. 501691) during storage with or without 3% w/w IMP, GMP, Inosine or nothing added. Note: the ordinate shows the pH measured after 6 hrs. of incubation at 30° C., amount of inoculation material: 0.01% w/v. A higher pH is indicative of less acidifying activity (i.e. less metabolic activity) of the culture. Solid diamond indicates addition of 3% w/w IMP, solid square indicates addition of 3% w/w GMP, solid triangle indicates addition of 3% w/w Inosine and a cross indicates that no cryoprotective additive were added.

Stability profiles for F-DVS™ FI-Da N given as acidification activity are summarized in FIG. 8.

It appears that the trend that was reported during the initial phase storage of the F-DVS™ FI-Da N can be extended to 21 or even 49 days. Also during prolonged storage Inosine seems to be a better cryoprotective of F-DVS™ FI-Da N than GMP which again is better that IMP. Furthermore this experiment indicates that the advantage of using of inosine as cryoprotective agent during the initial phase of storage also can be extended to the prolonged storage situation. Thus, the use of inosine as cryoprotective agent is expected to result in a product with an enhancement of more than twice the acidification activity even after prolonged storage.

This is an important result since average shelf life of commercial frozen cultures is 1 year.

Example 12

The Effect of Different Additives on the Stability on a Freeze-dried LD-culture of Fl-Da N This example describes the stability of freeze-dried LDultures (FD-DVS) of Fl-Da-N formulated with and without a number of different additives, which may act as cryprotective agents. In the experiments the concentration of the various additives were 3% w/w per gram concentrated biomass unless other vice indicated in the figures.

After fermentation, biomass was harvested and concentrated via centrifugation from fermentation broth of Fl-Da N as described in the Materials and Method section. The cell concentrate was divided into a number of portions and was added to each of the portions. To simulate the situation encountered in the industrial situation during a freezing process, the additives and concentrates were mixed and stored for 5 hours at 8° C. and subsequently frozen ditives and concentrates were mixed and stored for 5 hours at 8° C. and subsequently frozen in liquid nitrogen and further stored at −50° C. for one day before freezedrying. After freeze-drying was completed the culture was stored at −50° C. until analysis. The freeze-dried culture had a content of viable bacteria of at least $10^{10}$ colony forming units (CFU) per g freeze-dried material. Culture activity in milk (LAB-milk) was measured by the acidifying activity assay after 1 day and after 2 months of storage at −50° C.

Figure 9:
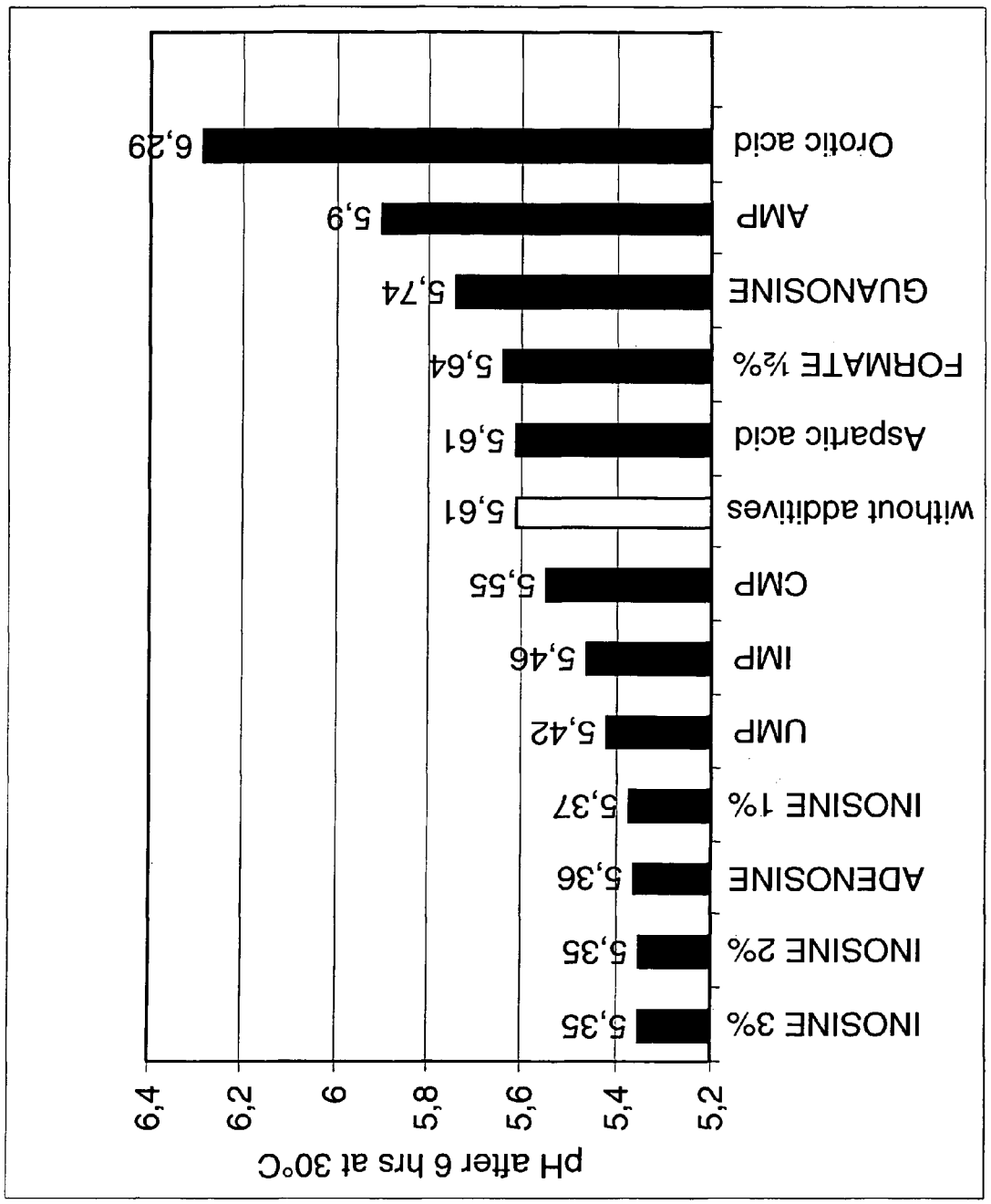
FIG. 9. Shows the storage stability expressed as the acidifying activity of freeze-dried concentrated culture Fl-Da N culture with and without various additives were added after 1 day of storage at −50° C. Note: the ordinate shows the pH measured after 6 hrs. of incubation at 30° C., amount of inoculation material: 0.005% w/v. A higher pH is indicative of less acidifying activity (i.e. less metabolic activity) of the culture. The result of the acidification assay is indicated for each additive. Most of the additives are purine bases, pyrimidine bases, nucleosides and nucleotides. IMP is brief for inosine-5'-monophosphate, AMP for adenosine-5'-monophosphate, UMP for uranosine-5'-monophosphate, CMP for cytidine-5'-monophosphate, MSG for monosodium glutamate. The percentages of the additive refer to % w/w of the additive added to the concentrated culture. Where no %-value is indicated 3% w/w was added.
Figure 10:
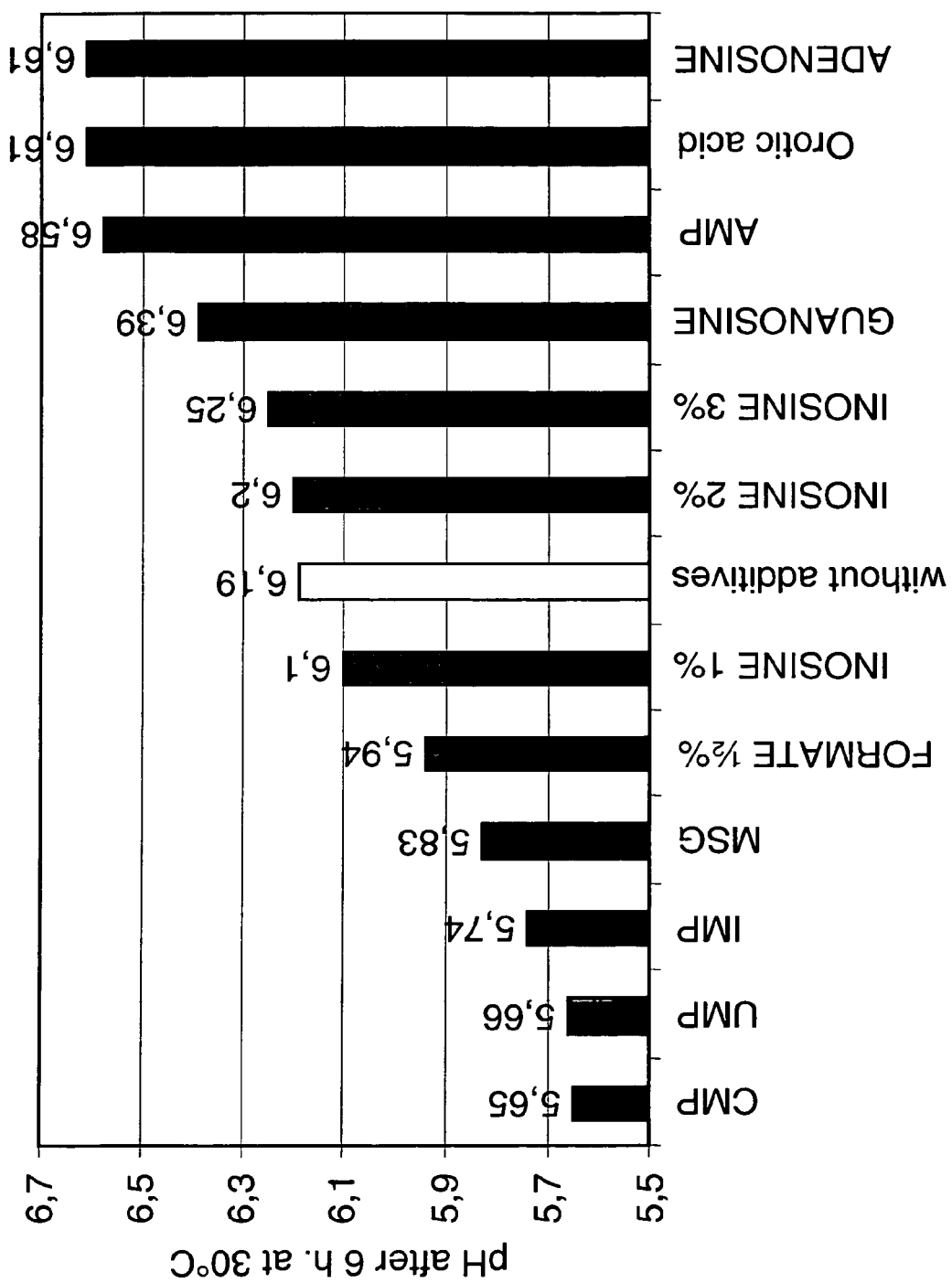
FIG. 10. Shows the storage stability expressed as the acidifying activity of freeze-dried concentrated culture Fl-Da N culture with and without various additives was added after 2 months of storage at −50°C. For further details see legend to FIG. 9.

Results are shown in FIGS. 9 and 10.

From this experiment it is clear that the different additives have a very different effect on the stability of a freeze-dried DVS Fl-Dn N culture. In addition this experiment shows that additives, which appear optimal in the initial phase of storage, not necessary are optimal during prolonged storage. This is illustrated by the effect of adding 3% w/w inosine or adenosine to cultures. Tested after only one day of storage at −50° C. it appears that both 3% w/w inosine and 3% w/w adenosine are highly efficient to ensure stability of the culture, but after 2 months of storage at −50° C. it was clear that 3% w/w CMP, UMP or IMP is preferred. Surprisingly; the result of the 2 months stability experiment −50° C. (FIG. 10) indicates that adenbsine is harmful to the culture. MSG (monosodium glutamate), which is a well-known cryoprotective agent, (Font de Valdez, 1983) is enclosed in the experiment for reasons of comparison. Further, it should be noted that the concentration of Na-formate is ½% w/w, because 3% w/w is detrimental for frozen cultures, see example 15 below.

Example 13

The Effect of a Combination of Additives on the Stability of a Frozen *L. bulgaricus* Culture Frozen with a Freezing Rate of 1° C. per min.

This example describes the effect of an addition of a combination of two potential cryoprotective agents (IMP and Inosine) on the activity implied by the manufacturing of a frozen *L. bulgaris* culture. In the example activities of cultures with and without such addition were compared.

The *L. bulgaricus* culture was cultured in MRS broth (Difco) for 12 hrs at 40° C. The culture was cooled to 12° C. and the pH of the culture was adjusted to 6,0. Following cooling, the bacteria in fermentation broths were concentrated 10-20 times by centrifugation, additives were added and subsequently slowly frozen in a freezer with controlled cooling ensuring a cooling-rate of approximately 1° C. per minute until −50° C. was reached. The cultures were stored at −50° C. until next day (approximately 18 hrs) before the acidification assay was performed. The acidification assay was performed as described in the Materials and Methods section except that the assay was based on a 0.02% w/w inoculum and performed at 40° C. for a period of 5 hours.

Figure 11:
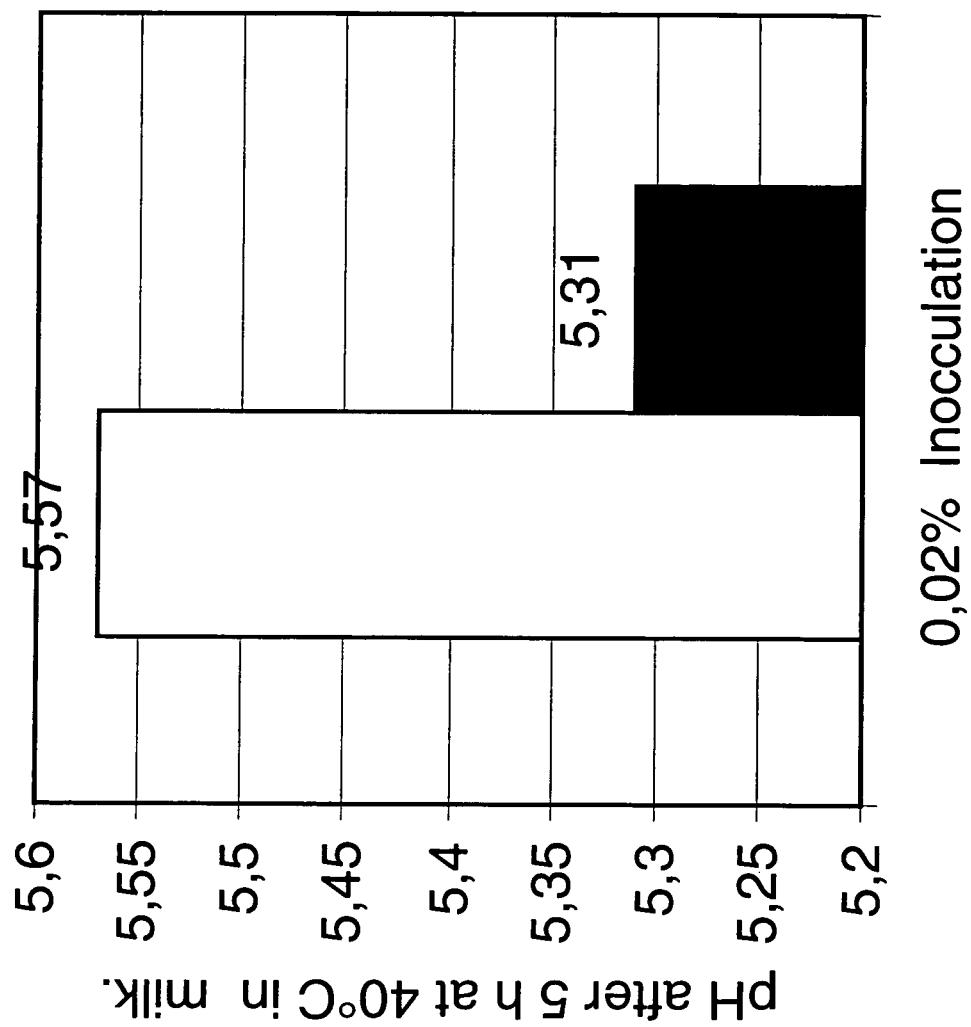
FIG. 11. Activity of Frozen *L. bulgaricus* with and without additives added (3% IMP+2% Inosine). Freezing rate around 1° C./min. Filled bar indicates culture where additives were added prior to freezing. The acidification assay was based on a 0.02% w/w innoculum and performed for 5 hrs at 40° C. A higher pH is indicative of less acidifying activity (i.e. less metabolic activity) of the culture.
Figure 12:
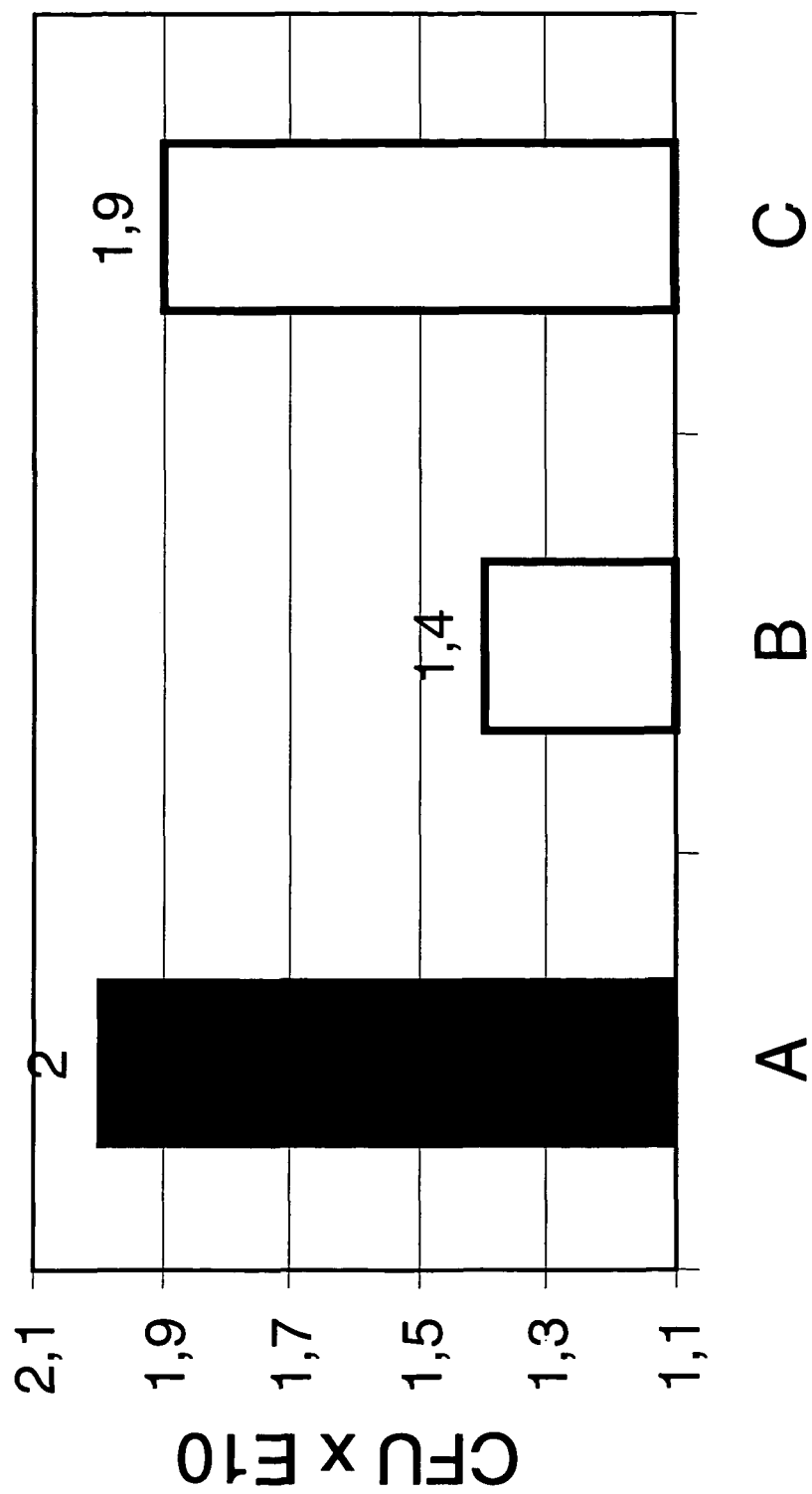
FIG. 12. Effect on viability of a quick-frozen *Bifidobacterium infantis* culture (A) compared to two *B. infantis* cultures that were slowly frozen (B and C). Culture C was added 3% w/w IMP and 2% w/w Inosine as cryoprotective agents. Freezing rate for culture B and C was 1° C./min, whereas culture A was frozen by dripping the cultures into liquid nitrogen.

In the experiment the 3% w/w IMP and 2% w/w inosine were added as cryoprotective, w/w refer to weight of additive per gram concentrated biomass. The IMP and inosine were added to the concentrate as an aqueous solution resulting in a 13% increase of the volume of the culture. This increase has not been accounted for in the data presented in FIG. 11. Thus the cryoprotective effect is even larger than indicated in the figure.

This experiment shows that a combination of two, additives according to the present invention, in casu 3% w/w IMP and 2% w/w Inosine, renders the culture considerably more stable. The difference in stability equals 0.26 pH units for the *L. bulgaricus* culture after storage for 1 day at −50° C. 0.26 pH units is nearly equal to a 50% difference in acidification activity (i.e. the stabilized culture is approximately 2 times as active as the unstabilized culture). This experiment furthermore show that the cryoprotective effect IMP and inosine can be extended also to comprise cultures that are slowly frozen.

Example 14

The Effect of a Combination of Additives on Viability of Frozen *B. Infantis*

This example explores the effect of a combination of 3% w/w IMP and 2% w/w Inosine on the stability of slowly frozen *Bifidobacterium infantis*.

The *Bifidobacterium infantis* culture was cultured in MRS broth (Difco). The culture was cooled to 12° C. and the pH of the culture was adjusted to 6,0. Following cooling, the bacteria in fermentation broths were concentrated 10-20 times by centrifugation, additives were added and subsequently the cultures were frozen either fast by dripping the concentrated culture into liquid, nitrogen (culture A) or slowly by cooling the culture in a freezer with controlled cooling ensunng a cooling rate of approximately 1° C. per minute until −50° C. was reached (culture B and C). The cultures were stored at −50° C. until next day (approximately 18 hrs) before the viability assay (CFU assay) was performed as described in the Materials and Methods.

This experiment showed that compared to a quickly frozen culture of *Bifidobacterium infantis* (culture A) the viability of a slowly frozen culture (B) is considerably reduced. Importantly, this experiment further indicates that if a combination of two additives according to the present invention, in casu 3% w/w IMP and 2% w/w Inosine, was added prior to freezing (culture C), then the number of CFU of the slowly frozen culture was almost identical to the quickly frozen culture.

We conclude that a combination of 3% w/w IMP and 2% w/w Inosine is effective as a cryoprotective additive for *B. infantis* that are slowly frozen.

Example 15

The Effect of Different Additives on the Stability on a Frozen Culture F-DVS™ CH-N 19

This example describes the stability of frozen direct vat set cultures (F-DVS™) of the CH-N 19 culture formulated with and without a number of different additives, which may act as cryoprotective agents.

After fermentation, biomass was harvested and concentrated via centrifugation from fermentation broth of F-DVS™ CH-N 19. The cell concentrate was divided into a number of portions the various additives were added as indicated in the figures. The concentration of the various additives is given in the figures as % w/w per gram concentrated biomass.

The additives and concentrates were mixed for 30 minutes, dropwise frozen in liquid nitrogen and subsequently stored at −50° C.

Figure 13:
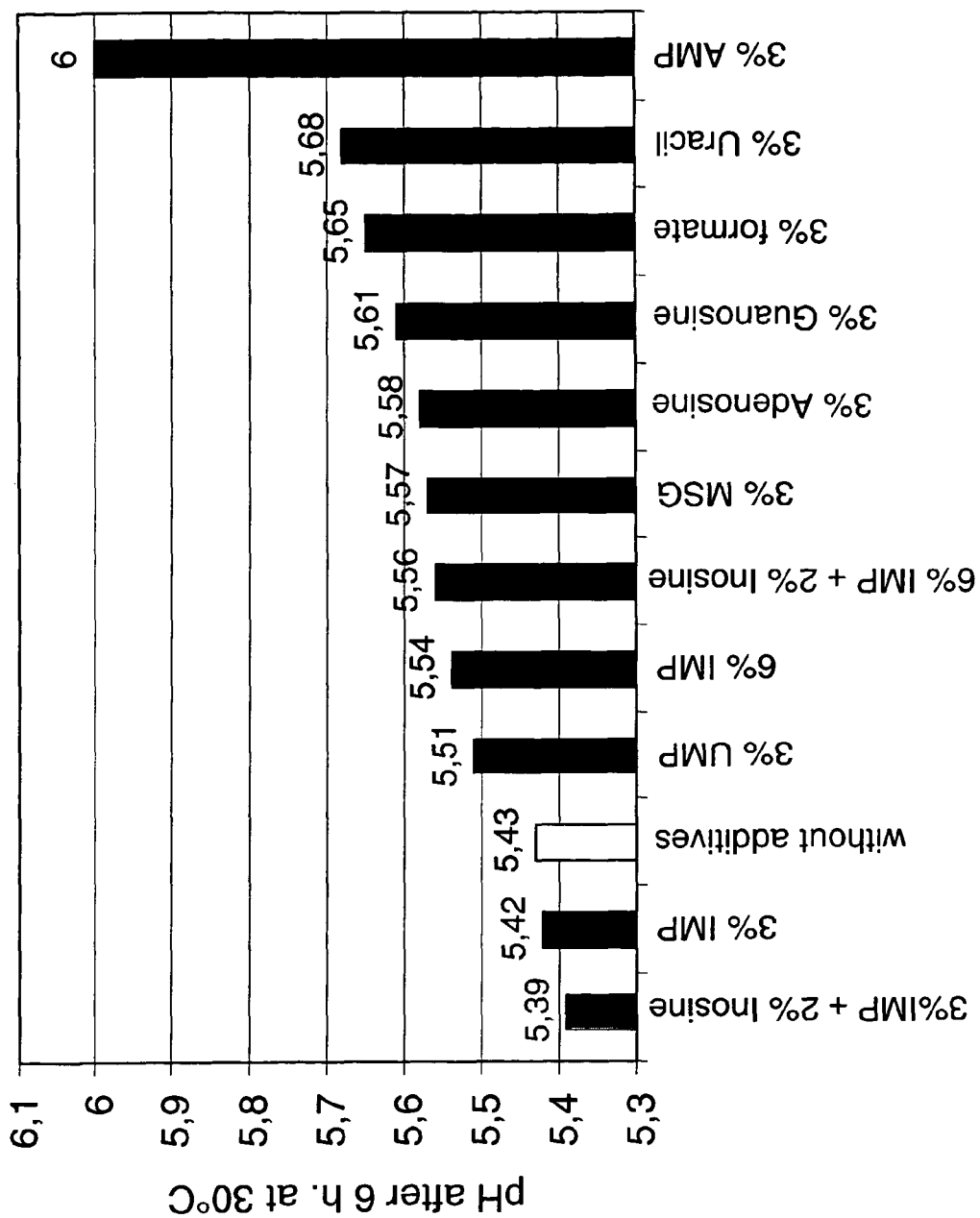
FIG. 13. Shows the storage stability expressed as the acidifying activity of quick frozen concentrated culture CH-N 19 culture with and without various additives were added after 1 day of storage at −50° C. Note: the ordinate shows the pH measured after 6 hrs. of incubation at 30° C., amount of inoculation material: 0.005% w/v. A higher pH is indicative of less acidifying activity (i.e. less metabolic activity) of the culture. The result of the acidification assay is indicated for each additive and combination of additives.
Figure 14:
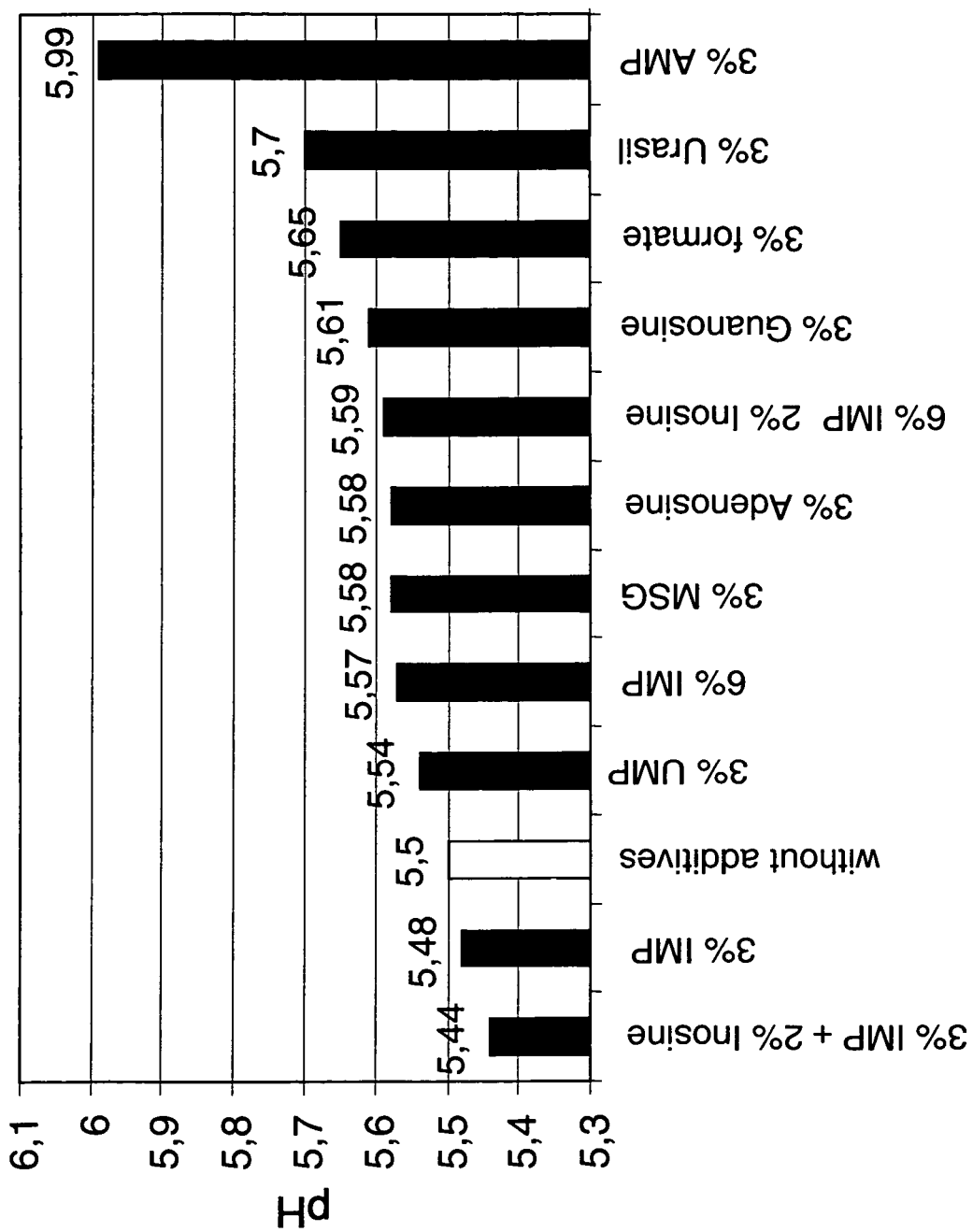
FIG. 14. Shows the storage stability expressed as the acidifying activity of quick frozen concentrated culture CH-N 19 culture with and without various additives were added after 6 days of storage at −50° C. Further details see legend to FIG. 13.

Culture activity in milk (LAB-milk) was measured as acidification activity after 1 day (FIG. 13) and 6 days (FIG. 14) of storage at −50° C. The activity assay is based on a 0,005% w/v inoculum and 6 hrs incubation at 30° C.

As seen in example 12 also this experiment showed that the various additives have a very different effect on the stability of a frozen culture. Interestingly, this experiment showed that both adenosine and adenosine-5'-monophosphate are harmful to the activity of the culture. The experiment also provided evidence that 3% w/w Na-formate is detrimental to the activity of frozen cultures.

Example 16

Trial with Addition of IMP and Inosine (From Example 15) with CH-N 19™ Added for the Production of Gouda 45+cheese Production of Gouda 45+ in 150 kg Cheese Vats
1. Milk
Raw milk was delivered from the Borup Dairy, Denmark, which had been pasteurized at ~72° C. for 15 sec (organic milk, 76-78C. for 15 sec) and then cooled to 5° C. The protein content will normally vary from 3.4-3.7% protein. The milk received was analyzed on the Milkoscanner(Foss Electric A/S, Hillerød, Denmark) for fat and protein %. The milk temperature was taken and a sample was taken for bacteriological analysis. The milk was stored in a cooling room until use.

2. Standardization
The milk for Gouda 45+ production should have a fat content of 3.00% (with a protein content of 3.4%), which in the final cheese will result in ~45% fat in dry matter. The fat-to-protein ratio was calculated using the stanidard methods of the art. The cheese milk was standardized by adding the calculated amounts of cream or skim milk. After standardization the milk was preheated in the heat exchanger to the pre-ripening temperature of 32° C. and pumped into the cheese vats. A slow agitation (235 rpm) was continued until rennet is dispersed in the milk.

3. CaCl2 and Saltpeter
Saltpeter was added in a concentration of 0.020%, being 30 g per 150 kg milk. CaCl2 was added to the milk in an amount of 0-20 g per 150 kg milk from a 34% solution if needed.

4. Culture
In this experiment, 4 batches. were produced and compared. In the first set of batches, one batch was inoculated with 0.005% F-DVS CH-N 19 with IMP and Inosine added before freezing (batch 1B). A reference batch culture was inoculated with 0.01% F-DVS CH-N 19 without IMP and Inosine added (batch 1A). A second set of batches was inoculated with 0.005% F-DVS CH-N 19 with IMP and Inosine added before freezing (batch 2B). A reference batch was inoculated with 0.01% F-DVS CH-N 19 without IMP and Inosine added (batch 2A). Before addition of rennet the culture is allowed to grow for 35 min at 32° C.

5. Rennet
Rennet CHY-MAX Plus (200 IMCU/mL) was added in the amount of 0.022% w/w (30.0 g per 150 kg). The rennet was diluted in 3 times its volume in clean cold tap water before use. Agitation (235 rpm) was continued for not more than 1 min after rennet addition and the agitator was removed from the vat. It appears that the milk has coagulated after 35 min. following the addtion of rennet.

Manufacture of Gouda 45+
Coagulation of the milk normally takes 30-45 min. The coagulum was cut by the frame cutter with 5 mm between the strings. The frame cutter was first run horizontally from end to end followed by a run vertically from end to end in the cheese vat. Then the coagulum was cut vertically from side to side three times down the sides of the vat until cubes of 5 mm were obtained. The curd was treated very carefully at this stage to minimize losses to the whey. The agitator was replaced into the vat and the curd was pre-stirred slowly (350 rpm) for 15-20 min. After 15-20 min 45 kg of whey was drainedoff and the agitator was then adjusted to a faster stirring level for 20 min (415 rpm). The scalding was then started by raising the temperature to 38° C. in the first set of batches and 40° C. for the second set of batches within 20 min. A slow, steady and controlled temperature increase was required. After reaching 38° C. or 40° C., the stirring was carried on with a total stirring of 85 min (meaning 35-45 min. at 38° C. or 40° C.).

6. Pressing
After 95 min of stirring the agitator was removed and the curd was allowed to settle in the vat. The curd was then pitched and pre-pressed using the pre-pressing-plates and the hydraulic cylinders to apply a pressure of 2.5 bar to the curd for 30 min. After pre-pressing the curd was cut into two blocks. The cheese blocks were placed in appropriate moulds (30×30 cm) with the same side downwards as during the pre-pressing. The moulds were then placed in the pressing unit and pressed for 20 min at 2 bar and subsequently for 1-2 hour at 4-6 bar. After end of pressing the height of the cheeses was measured, the cheeses were weighed, identified, and the pH was analyzed. Finally, the cheeses were stored in the moulds until they reached pH 5.7, and after that they went directly to salting in brine.

7. Salting

Salting was carried out for 20-24 hours in a brine of 20% NaCl+0.25% CaCl2, at a temperature of 10-12° C. to reach a salt content of about 1.7% in the final cheeses. It was important that the cheeses were properly separated and submerged during the brine salting to obtain the desired salt content. After salting the cheeses were dried for 1-2 hours before packaging.

8. Packaging

Before packaging the cheeses were sprayed with Natamycin (300 ppm in water), then vacuum-packed in Cryovac® plastic bags (BK1L) and put into hard plastic boxes (30×30 cm). After packaging the boxes were stored at 14 C. for 4 weeks, and after that they were stored at 5-8C.

Culturing Conditions:

Batch 1:

A.) Experimental Culture F-DVS CH-N 19 with IMP and Inosine added.
Scalding temperature of 38° C. Inoculation 0.005%

| Treatment | Time | | Temperature | | Stirring speed | | | |
|---|---|---|---|---|---|---|---|---|
| Batch no. | Set to | Actual | Set to | Actual | Set to | Actual | pH | Titer |
| Add milk | 09:30 | | | 32.0 | 235 | | 6.64 | |
| Add saltpeter | 09:35 | | | | | | | |
| Add culture | 09:45 | | | | | | | |
| Add adjuncts | 10:15 | | | | | | | |
| Add rennet | 10:20 | | | | | | 6.55 | |
| Cutting | 10:55 | | | | | | | |
| Pre-stirring | 11:00 | | | | 350 | | | |
| Whey off | 11:20 | | | 32.0 | | | 6.53 | 0.14 |
| Middle-stirring | 11:25 | | | | 390 | | | |
| Scald start/stirring | 11:35 | | | | | | 6.52 | 0.14 |
| Scalding end | 11:50 | | | 38.0 | 390 | | 6.51 | 0.15 |
| End of stirring | 12:30 | | | | | | 6.48 | 0.16 |
| Pre-pressing | 12:35 | | | | | | | |
| Pre-pressing end | 13:05 | | | | | | 6.34 | 0.17 |
| Filling in moulds | 13:10 | | | | | | | |
| Pressing 1 | 13:15 | | | | | | | |
| Pressing 2 | 13:45 | | | | | | | |
| Pressing 3 | 15:15 | | | | | | | |
| Pressing end | 15:15 | | | | | | | |
| pH after 6 hours | 15:45 | | | | | | 5.75 | |
| In water | 16:00 | | | | | | | |
| In Brine | 17:15 | | Brine: 21% NaCl, pH 5.2, temp: 11.5° C. | | | | 5.48 | |
| Out Brine | 15:45 | | 22.5 h | | | | | |
| Prepress | | | 2.5 bar 30 min | | | | | |
| pH after 30 hours | | | | | | | 5.21 | |

B.) Reference Culture F-DVS CH-N 19 without IMP and Inosine added.
Scalding temperature of 38° C. Inoculation 0.01%

| Treatment | Time | | Temperature | | Stirring speed | | | |
|---|---|---|---|---|---|---|---|---|
| Batch no. | Set to | Actual | Set to | Actual | Set to | Actual | pH | Titer |
| Add milk | 09:00 | | | 32.0 | 235 | | 6.63 | |
| Add saltpeter | 09:05 | | | | | | | |
| Add culture | 09:15 | | | | | | | |
| Add adjuncts | 09:45 | | | | | | | |
| Add rennet | 09:50 | | | | | | 6.57 | |
| Cutting | 10:25 | | | | | | | |
| Pre-stirring | 10:30 | | | | 350 | | | |
| Whey off | 10:50 | | | 32.0 | | | 6.53 | 0.15 |
| Middle-stirring | 10:55 | | | | 390 | | | |
| Scald start/stirring | 11:05 | | | | | | 6.52 | 0.15 |
| Scalding end | 11:20 | | | 38.0 | 390 | | 6.52 | 0.15 |
| End of stirring | 12:00 | | | | | | 6.51 | 0.16 |
| Pre-pressing | 12:05 | | | | | | | |
| Pre-pressing end | 12:35 | | | | | | 6.41 | 0.17 |

B.) Reference Culture F-DVS CH-N 19 without IMP and Inosine added.
Scalding temperature of 38° C. Inoculation 0.01%

| Treatment | Time | | Temperature | | Stirring speed | | | |
|---|---|---|---|---|---|---|---|---|
| Batch no. | Set to | Actual | Set to | Actual | Set to | Actual | pH | Titer |
| Filling into moulds | 12:40 | | | | | | | |
| Pressing 1 | 12:45 | | | | | | | |
| Pressing 2 | 13:15 | | | | | | | |
| Pressing 3 | 14:45 | | | | | | | |
| Pressing end | 14:45 | | | | | | | |
| pH after 6 hours | 15:15 | | | | | | 5.92 | |
| In water | 15:30 | | | | | | | |
| In Brine | 16:45 | | Brine: 21% NaCl, pH 5.2, temp: 11.5° C. | | | | 5.70 | |
| Out Brine | 15:15 | | 22.5 h | | | | | |
| Prepress | | | 2.5 bar 30 min | | | | | |
| pH after 30 hours | | | | | | | 5.20 | |

Reference CHN-19 1A (column header above table)

Batch 2:

A.) Experimental Culture F-DVS CH-N 19 with IMP and Inosine added.
Scalding temperature of 40° C. Inoculation 0.005%

CH-N19 with IMP and Inosine 2B

| Treatment | Time | | Temperature | | Stirring speed | | | |
|---|---|---|---|---|---|---|---|---|
| Batch no. | Set to | Actual | Set to | Actual | Set to | Actual | pH | Titer |
| Add milk | 08:30 | | 32.0 | | 235 | | 6.63 | |
| Add saltpeter | 08:35 | | | | | | | |
| Add culture | 08:45 | | | | | | | |
| Add adjuncts | 09:15 | | | | | | | |
| Add rennet | 09:20 | | | | | | 6.54 | |
| Cutting | 09:55 | | | | | | | |
| Pre-stirring | 10:00 | | | | 350 | | | |
| Whey off | 10:20 | | 32.0 | | | | 6.52 | 0.14 |
| Middle-stirring | 10:25 | | | | 390 | | | |
| Scald start/stirring | 10:35 | | | | | | 6.52 | 0.15 |
| Scalding end | 10:50 | | 40.0 | | 390 | | 6.50 | 0.15 |
| End of stirring | 11:30 | | | | | | 6.47 | 0.16 |
| Pre-pressing | 11:35 | | | | | | | |
| Pre-pressing end | 12:05 | | | | | | 6.36 | 0.16 |
| Filling in moulds | 12:10 | | | | | | | |
| Pressing 1 | 12:15 | | | | | | | |
| Pressing 2 | 12:45 | | | | | | | |
| Pressing 3 | 14:15 | | | | | | | |
| Pressing end | 14:15 | | | | | | | |
| pH after 6 hours | 14:45 | | | | | | | 6.02 |
| In water | 16:00 | | | | | | | |
| In Brine | 19:00 | | | | | | 5.60 | |
| Out Brine | 17:30 | | 22.5 h | | | | | |
| Prepress | | | 2.5 bar 30 min | | | | | |
| pH after 30 hours | | | | | | | 5.22 | |

B.) B.) Reference Culture F-DVS CH-N 19 without IMP and Inosine added.
Scalding temperature of 40° C. Inoculation 0.01%

Reference CHN-19
2A

| Treatment | Time | | Temperature | | Stirring speed | | | |
|---|---|---|---|---|---|---|---|---|
| Batch no. | Set to | Actual | Set to | Actual | Set to | Actual | pH | Titer |
| Add milk | 08:00 | | | 32.0 | 235 | | 6.60 | |
| Add saltpeter | 08:05 | | | | | | | |
| Add culture | 08:15 | | | | | | | |
| Add adjuncts | 08:45 | | | | | | | |
| Add rennet | 08:50 | | | | | | 6.54 | |
| Cutting | 09:25 | | | | | | | |
| Pre-stirring | 09:30 | | | | 350 | | | |
| Whey off | 09:50 | | | 32.0 | | | 6.54 | 0.14 |
| Middle-stirring | 09:55 | | | | 390 | | | |
| Scald start/stirring | 10:05 | | | | | | 6.53 | 0.14 |
| Scalding end | 10:20 | | | 40.0 | 390 | | 6.51 | 0.14 |
| End of stirring | 11:00 | | | | | | 6.49 | 0.15 |
| Pre-pressing | 11:05 | | | | | | | |
| Pre-pressing end | 11:35 | | | | | | 6.41 | 0.16 |
| Filling in moulds | 11:40 | | | | | | | |
| Pressing 1 | 11:45 | | | | | | | |
| Pressing 2 | 12:15 | | | | | | | |
| Pressing 3 | 13:45 | | | | | | | |
| Pressing end | 13:45 | | | | | | | |
| pH after 6 hours | 14:15 | | | | | | 6.24 | |
| In water | 15:30 | | | | | | | |
| In Brine | 19:00 | | Brine: 21% NaCl, pH 5.2, temp: 11.5° C. | | | | 5.84 | |
| Out Brine | 17:30 | | 22.5 h | | | | | |
| Prepress | | | 2.5 bar 30 min | | | | | |
| pH after 30 hours | | | | | | | 5.32 | |

Results:

The cheeses were evaluated after 8 weeks. The chemical analysis was determined to ensure that the cheese was within the requirements of this kind of cheese (moisture, salt, fat) 4 weeks old. A sensory evaluation of the cheeses was also conducted to ensure that it had the right eye formation, texture and flavor.

The cheese products were further analyzed for the following defects:

1.) Defects in exterior (form, rind, color, smell).
2.) Defects in interior (color, structure, consistency).
3.) Defects in smell and taste.

The batches were then scored using one of the numbers: 0, 3, 6, 8, 9, 10, 11, 12 or 13. The scores of 13 is the best.
Batches 1
1A.) Reference.Vat 406 F-DVS CHN-19 Scalding temperature of 38 C.
  The eye formation was good, 11.
  The smell was good, nice and clean, character 11.
  The taste was as desired of Gouda, very good, 11 (buttery, a little sour salty and nutty).
1B.) Vat 407 F-DVS CHN-19 added INP and Inosine. Scalding temperature of 38 C.
  The eye formation was good, 11.
  The smell was good, nice and clean, character 11.
  The taste was as desired of Gouda, very good, 11 (buttery, a little sour salty and nutty)
  No difference in the cheeses from the existing culture and the tested culture was detected.
Batches 2
2A.) Reference Vat 404 F-DVS CH-N 19. Scalding temperature of 40 C.
  Did not quite have the desired eye formation; the eyes were too small, character 9.
  The smell was good, nice and clean, character 11.
  The taste was as desired of Gouda, maybe a little too salty but very good, 11.
2B.) Vat 405. F-DVS CH-N 19 with IMP and Inosine. Scalding temperature of 38 C.
  The eye formation a little better than the. other but still we desire bigger holes, 10.
  The smell was good, nice and clean, character 11.
  The taste was as desired of Gouda, maybe a little too salty but very good, 11.
  No difference in the cheeses from the existing culture and the tested culture was detected.

Example 17

Trial with Addition of IMP and Inosine to F-DVS R-604 for the Production of Cheddar Cheese Standard Instruction for Production of Cheddar Cheese in 150 kg Cheese Vats Cheddar is one of the most widely produced cheeses. Originally it was only made in the UK but is now made all over the world, predominantly in Australia, Canada, Ireland, New Zealand and the USA. The basic principles of Cheddar cheesemaking remain the same in all countries with only a few modifications.

The colour may range from pale cream to deep yellow. Annatto is added in some cases to give an orange/red colour. The texture is firm and close, and the cheese does not crumble when cut. Most Cheddar is sold when it has matured for 3-5 months, and it is very mild. Good mature Cheddar has a nutty flavor with adistinctive bite and is best matured after 9-12 months.

This procedure describes the traditional Cheddar making procedure, and serves to determine the effects of cryopreservation with IMP and Inosine on the culture inoculum.

3. Milk

Milk is ordered from Borup Dairy (Denmark) and delivered as raw milk, which is pasteurized at approximately 72° C. (162° F.) for 15 sec, and then cooled to about 30-32° C. 475-600 ml of Chr. Hansen's Annatto A320WS is added per 5000 l of milk where coloured Cheddar is desired. Parallel batches of culture are prepared to compare the effects of cryopreservation in the presence of IMP and Inosine on F-DVS R-604.

4. Culture

A control culture of F-DVS R-604 cryopreserved without IMP and Inosine (Batch 1) is added as inoculum at a concentration of about 750 g/5000 liters of culture. A test culture of F-DVS R-604 cryopreserved with IMP and Inosine (Batch 2) is added as inoculum at a concentration of about 500 g/5000 liters of culture.

5. Rennet

Rennet CHY-MAX Powder Extra is added to each of the batches in the amount of 2.5-3 g per 100 l of milk. Following the addition of Rennet, a gel will form within 30-45 minutes.

6. Manufacture of Cheddar cheese

The following procedure is followed as closely as possible for each of the batches tested. The curd is cut into small cubes of 5×5 mm. The temperature is then raised to about 38-40° C. over a 40-50 min period. The curd and the whey are stirred for 30-50 minutes depending on the moisture content required.

7. Cheddaring

The curd and whey are separated and the curd is allowed to fuse. The curd is then "Cheddared". The fused curd is cut into blocks, which are turned every 10-15 minutes. When the acidity of the whey from the blocks reaches pH 5.5-5.6, the curd is milled. Milling involves cutting the large curd blocks into finger-sized pieces.

8. Salting

Approximately 2% salt is added to the curd, giving a final salt concentration in the cheese of 1.6-1.8% (Salt in moisture 4.5-5%).

9. Packaging

Moulding and pressing takes place in a tower under partial vacuum, with a sharp mechanical pressing. The cheese is formed in 20 kg blocks and vacuum packed in plastic bags. The cheese is ripened at 7-10° C. for 3-12 months, depending on the strength of flavour required (i.e., mild or mature).

Conclusion

The Cheddar cheese produced from each of the batches will be compared for taste, texture and other qualities to determine whether the use of inoculum cryopreserved with IMP and Inosine influences the final Cheddar cheese product. Inoculum containing a mixture of IMP and Inosine will produce practically the same quality of cheese as an inoculum lacking a mixture of IMP and Inosine. A further advantage of the invention is that a reduced quantity of concentrated inoculum may be used if the inoculum contains an admixture of IMP and Inosine.

Example 18

Trial with Addition of IMP and Inosine to F-DVS ST-M3 for the Production of Cottage Cheese Standard Instruction for Production of Cottage Cheese in 150 kg Cheese Vats Cottage cheese is a very popular low fat soft cheese in weight conscious UK and the USA. Plain cottage cheese is very bland so it is popular to flavour the product by adding chives, onions, etc. Two methods of manufacturing of cottage cheese are used: a short set method and a long set method. Details of both are provided. The short set method is described immediately, followed by the long set method which is described in section five.

1. Milk

Milk is ordered from Borup Dairy (Denmark) and delivered as raw milk, which is pasteurized at approximately 72° C. (162° F.) for 15 sec, and then cooled to about 34° C.

2. Culture

For the short set method, a control culture of F-DVS ST-M3 cryopreserved without IMP and Inosine (Batch 1) is added as inoculum at a concentration of about 2500 g/5000 liters of culture. A test culture of F-DVS ST-M3 cryopreserved with IMP and Inosine (Batch 2) is added as inoculum at a concentration of about 2000 g/5000 liters of culture.

3. Rennet

Rennet CHY-MAX Powder Extra is added to each of the batches in the amount of 0.2-0.5 g per 5000 l of milk.

4. Manufacture of Cottage Cheese

The following procedure is followed as closely as possible for each of the batches tested. The milk is incubated for 4.5-5 hours until a pH of 4.65-4.8 is reached. The curd is cut into even cubes of about 12 mm. The curd rests for 10-15 minutes. The curd is stirred very gently, and scalding is commenced to a temperature of 55-58 ° C. which is achieved in 60-75 minutes. When the curd is sufficiently firm, the whey is drained off. The curd is then washed and drained three times as follows:

First, wash with water (13-15° C.) to lower the curd temperature to 29-32° C. Second, wash with water (13-15° C.) to lower the curd temperature to 18° C. Finally, wash with water (2-5° C.) to lower the curd temperature to 2-5° C. After the final draining, the curd is ready to be blended with a sweet or cultured dressing. Dressings may be made from various combinations of cream, milk and skim milk powder.

5. Long Set Method

The process is similar to the one which may be used in the short set method, except for the inoculation concentration of culture, the incubation temperature and incubation time. For the long set method, a control culture of F-DVS ST-M3 cryopreserved without IMP and Inosine (Batch 1) is added as inoculum at a concentration of about 500 g/5000 liters of culture. A test culture of F-DVS ST-M3 cryopreserved with IMP and Inosine (Batch 2) is added as inoculum at a concentration of about 300 g/5000 liters of culture. The lower inoculation concentration and incubation temperature of 20-22° C. will result in a longer incubation time needed to achieve the desired end pH, which will normally take 14-18 hours.

Conclusion

The Cottage cheese produced from each of the batches will be compared for taste, texture and other qualities to determine whether the use of inoculum cryopreserved with IMP and Inosine influences the final Cottage cheese product. Inoculum containing a mixture of IMP and Inosine will produce practically the same quality of cheese as an inoculum lacking a mixture of IMP and Inosine. A further advantage of the invention is that a reduced quantity of concentrated inoculum may be used if the inoculum contains an admixture of IMP and Inosine.

Example 19

Trial with Addition of IMP and Inosine to F-DVS ST-M3 for the Production of Mozzarella/Pizza Cheese Standard Instruction for Production of Mozzarella/Pizza Cheese in 150 kg Cheese Vats This type of Mozzarella is mostly used as Pizza cheese. As it is firmer than Soft Cheese Mozzarella it is easier to grate.

There are various types of Mozzarella which have different contents of water and fat in dry matter. Part skim, low-moisture Mozzarella is normally used as Pizza Cheese. Most often the curd is fermented to pH 5.0-5.2 before the curd is mixed with hot water and stretched. The choice of culture has a major influence on the characteristics of Pizza Cheese (i.e., stretching, browning, melting and oiling off).

1. Milk

Milk is ordered from Borup Dairy (Denmark) and delivered as raw milk, which is pasteurized at approximately 72° C. (162° F.) for 15 sec, and then cooled to about 36-38° C.

2. Culture

A control culture of F-DVS ST-M3 cryopreserved without IMP and Inosine (Batch 1) is added as inoculum at a concentration of about 750 g/5000 liters of culture. A test culture of F-DVS ST-M3 cryopreserved with IMP and Inosine (Batch 2) is added as inoculum at a concentration of about 500 g/5000 liters of culture. The culture is incubated for 30-45 minutes at 35-38° C.

3. Rennet

Rennet CHY-MAX Powder Extra is added to each of the batches in the amount of 1-3 g per 100 l of milk.

4. Manufacture of Mozzarella cheese

The following procedure is followed as closely as possible for each of the batches tested. The coagulum is cut into 5-8 mm cubes, and is allowed to heal for 5 minutes. The temperature is then increased to 40-43° C. for 15-20 rinutes with stirring. The cheese is then handled using the Cheddar curd method, where all of the whey is drained, the curd is cut into blocks and the blocks are turned during fermentation. Milling of the curd occurs at pH 5-5.25. When the desired pH is obtained, the cheese is placed in a stretching machine and mixed with hot water, 75-80° C. The process will take about 10-15 minutes, and the temperature of the curd reaches approximately 58-65° C. The stretched cheese, is moulded and immediately cooled in chilled water to 5-10° C., which will stop further acidification. Brine the cheese in a saturated salt brine at a temperature of 10° C. or lower.

The Mozzarella/Pizza cheese produced from each of the batches will be compared for taste, texture and other qualities to determine whether the use of inoculumcryopreserved with IMP and Inosine influences the final Mozzarella/Pizza cheese product. Inoculum containing a mi xture of IIP and Inosine will produce practically the same quality of cheese as an inoculum lacking a mixture of IMP and Inosine. A further advantage of the invention is that a reduced quantity of concentrated inoculum may be used if the inoculum contains an admixture of IMP and Inosine.

Example 20

Trial with Addition of IMP and Inosine to F-DVS CH-N 11 for the Production of Maasdammer Cheese Standard Instruction for Production of Maasdanuner Cheese in 150 kg Cheese Vats Maasdammer is a Swiss cheese type, named after the river Maas in the Netherlands. The cheese has a relatively large eye formation as well as a mild and nutty flavour due to the propionic acid bacteria added.

1. Milk

Milk is ordered from Borup Dairy (Denmark) and delivered as raw milk, which is pasteurized at approximately 72° C. (162° F.) for 15 sec or heat-treated at 65-70° C. for 20 seconds, and then cooled to about 30-32° C.

2. Culture

A control culture of F-DVS CH-N 11 cryopreserved without IMP and Inosine (Batch 1) is added asinoculum at a concentration of about 750 g/5000 liters of culture. A test culture of F-DVS CH-N 11 cryopreserved with IMP and Inosine (Batch 2) is added as inoculum at a concentration of about 500 g/5000 liters of culture. The culture is incubated for 10-40 minutes at 32° C.

3. Rennet

Rennet CHY-MAX Powder Extra is added to each of the batches in the amount of 1-3 g per 100 l of milk.

4. Manufacture of Maasdammer Cheese

A gel will form in about 30-45 minutes. The coagulum is cut into 5-7 mm cubes, and the curd is slowly stirred for 15-25 minutes. Approximately 35-45% of the whey is drained off and the curd is gently stirred for 15 minutes. Approximately 15-20% (of the start volume) hot water at approximately 60° C. is added. The temperature of the curd is about 35-38° C., and is stirred for about 30-45 minutes. Most of the whey is drained, and the curd is lightly pressed at 2-4 kg/cm$^2$ under the remaining whey for 15-30 minutes. The curd is cut into suitably sized blocks which are fitted into moulds. The moulds are lightly pressed for 20 minutes, followed by pressing at 4-6 kg/cm$^2$ for 1-2 hours. The curd blocks are dumped directly into cold brine at a pH of 5.6-5.7, and the target salt concentration of the cheese is 1-1.5%.

The Maasdammer cheese produced from each of the batches will be compared for taste, texture and other qualities to determine whether the use of inoculum cryopreserved with IMP and Inosine influences the final Massdammer cheese product. Inoculum containing a mixture of IMP and Inosine will produce practically the same quality of cheese as an inoculum lacking a mixture of IMP and Inosine. A further advantage of the invention is that a reduced quantity of concentrated inoculum may be used if the inoculum contains an admixture of IMP and Inosine.

Example 21

Trial with Addition of IMP and Inosine to F-DVS CHN-12 for the Production of Brie/Camembert Cheese Standard Instruction for Production of Brie/Camembert Cheese in 150 kg Cheese Vats Stabilised Brie/Camembert differs from Traditional Brie/Camembert in that softening of the cheese core is not so time dependent as the pH min, in the end of the curd manufacture, is 4.9-5.4 compared to 4.6-4.8 for Traditional Brie/Camembert. White moulds are used to give cheese its characteristic, white surface and its taste. There are two primary way of stabilising the pH of cheese:

1.) Stabilised—Washing the curd, i.e., removing lactose and thereby reducing the amount of sugar available for conversion to lactic acid. This helps to achieve the desired high pH. For Stabilised Brie/Camembert both mesophilic and thermophilic cultures are used, normally at 30% mesophilic and 70% thermophilic.

2.) Solubilised—Inhibition of starter when pH is close to the desired level, e.g., by salting or cooling. This type is only made with thermophilic cultures, as they are more sensitive to lower temperatures than mesophilic cultures.

1. Milk

Milk is ordered from Borup Dairy (Denmark) and delivered as raw milk, which is pasteurized at approximately 72° C. (162° F.) for 15 sec, and then cooled to about 35-37° C.

2. Culture

A control culture of F-DVS CHN-12 cryopreserved without IMP and Inosine (Batch 1) is added as inoculum at a concentration of about 250 g/5000 liters of culture. A test culture of F-DVS CHN-12 cryopreserved with IMP and Inosine (Batch 2) is added as inoculum at a concentration of about 200 g/5000 liters of culture. Into the mould is introduced 3-5 u of liquid PCa 1, PCa 3 or PCa FD per 1000 liters, as well as 0.5-1 u of GEO CD1.

3. Rennet

Rennet CHY-MAX Powder Extra is added to each of the batches in the amount of 2.5-3 g per 100 l of milk.

4. Manufacture of Brie/Camembert Cheese

A gel will form in about 30-45 minutes. The coagulum is cut into 10 mm cubes, and 40% of the whey is drained. The same volume of water is added at about 40-45° C. The culture is allowed to stand for 30-50 minutes with occasional, gentle stirring. The curd is ladled from the vat into the mould, and the mould is turned first after one hour, turned a second time after three hours, and turned a third time after eight hours. The curd is removed from the mould and immersed in 18% brine. The cheese is sprayed with 1-2 u of PCa 1, PCa 3 or PCa FD per 100 kilograms of cheese. The cheese ripens at 14-15° C. and 85% relative humidity for one day, then at 12° C. and 95% relative humidity for 8-10 days. When the mould growth is satisfactory, the cheese surface is dried, packed and stored at 4° C. Each cheese is packed in grease-proof paper and placed in a cardboard or chip box.

The Brie/Camembert cheese produced from each of the batches will be compared for taste, texture and other qualities to determine whether the use of inoculum cryopreserved with IMP and Inosine influences the final Brie/Camembert cheese product. Inoculum containing a mixture of IMP and Inosine will produce practically the same quality of cheese as an inoculum lacking a mixture of IMP and Inosine. A further advantage of the invention is that a reduced quantity of concentrated inoculum may be used if the inoculum contains an admixture of IMP and Inosine.

Example 22

Trial with Addition of IMP and Inosine to DVS™ FD-N for the Production of Cultured Buttermilk in 3-liter Scale Cultured Buttermilk
Suggested Recipe
Pre-treatment High quality, standardized homogenized milk with 0.5% fat was pretreated by pasteurization at 90° C. for 20 min in a Vat.

3% IMP. w/w and 2% Inosine were added as stabilizers to concentrated cultures of DVS FD-N, which mixture was then frozen. The name of the frozen product is now F-DVS™ FD-N.

Cultures of F-DVS™ FD-N were frozen without IMP and Inosine for control. All F-DVS™ cultures were stored for two months at −50° C. prior to use.

Concentrated cultures of (DVS FD-N) containing IMP and Inosine were used to inoculate the milk at a concentration of 0.005% and the milk was cultured at a temperature of 25° C. to a pH of approximately 4.5 in a 3 liter fermenter. Control cultures of DVS™ FD-N, frozen without IMP and Inosine, were used to inoculate the milk at a concentration of 0.01% and the milk was cultured at a temperature of 25° C. to a pH of approximately 4.5 in a 3 liter fermenter.

| Test no. | Culture | Amount of inoculant | Fermentation time | To pH |
|---|---|---|---|---|
| 1 | FD-N with IMP and Inosine | 0.005% | 15½ | 4.51 |
| 2 | FD-N without IMP and Inosine | 0.01% | 15½ | 4.51 |

Post Treatment

When pH reached 4.51, the product was stirred in a bucked with a handstirrer first and then for 1 min at voltage 55 with Ystral mixer. After stirring, the bucket was placed in cooling bath and cooled till 18° C. under periodical stiffing with a handmixer. The product was then poured into bottles and stored at 8° C.

Results:

The cultured buttermilk was tested for appropriate flavor on days 1 and 8:

| Day 1: | |
|---|---|
| FD-N with IMP and Inosine: | Fresh, low CO2, good aroma |
| FD-N without IMP and Inosine: | Fresh, low CO2, good aroma |

| Day 8: | |
|---|---|
| FD-N with IMP and Inosine: | Fresh, low CO2, good aroma |
| FD-N without IMP and Inosine: | High mouth feel, fresh, low CO2, good aroma |

The same fermentation times and pH were used for an inoculum of 0.005% F-DVS FD-N with IMP and Inosine added, compared with an inoculum of 0.01% F-DVS without IMP and Inosine. The addition of IMP and Inosine did not yield any change in the viscosity or the aroma/flavor of the cultured buttermilk.

It appears that the amount of inoculation material can be halfed if a mixture of IMP and Inosine has been added to the inoculation material in comparison with an inoculating material without IMP and Inosine. A similar quality of cheese in terms of taste and texture was produced using either the experimental inoculum or the control inoculum.

REFERENCES

M. R. Adams and M. O. Moss (2000) Food Microbiology, second edition, The Royal Society of Chemistry, UK, pp. 480, ISBN: 0-85404-611-9.

J. K. Andersen, B. Fabech, B. L. Jacobsen, H. Mejborn and L. Rasmussen (1997) Biokon-taminering, Veterinaær- og fødevaredirektoratet, København, Denmark.

P. Mazur. (1961) Physical and temporal factors involved in the death of yeast at subzero tem-peratures. Biophys J. (1): 247-64.

E. W. Nielsen and J. A. Ullum (1999). Mejerilaære 1, Erhvervsskolernes Forlag, Odense, Denmark.

G. Font de Valdez et al. (1983) Comparative study of the efficiency of some additives in protecting lactic acid bacteria against freeze-drying. Cryobiology;20(5):560-6.

A. White, P. Handler and E. L. Smith (1973) Principles of Biochemistry, 5'th ed., McGrawHill Kogakusha, Tokyo.

R. Scott, (1986), Cheesemaking process, second ed., Elsevier Applied Science Publishers, London and New York G. Bylund, (1995), Dairy processing handbook, Tetra Pak Processing Systems, Lund, Sweden F. Kosikowski, (1982), Cheese and fermented milk foods, second ed., Kosikowski & Associates, New York R. Scott (1986), Cheesemaking Practice, Second edition, Elsevier Applied Science Publishers, London and New York Gösta Bylund, MSc (1995), Dairy Processing Handbook, Tetra Pak Processing Systems, S-221 86 Lund, Sweden Frank Kosikowski (1982), Cheese and Fermented Milk Foods (2$^{nd}$ Ed), Published by Kosikowski & Associates, New York

The invention claimed is:

1. A stable non-liquid frozen or freeze-dried starter culture comprising:
    (a) a microorganism selected from the group consisting of *Bifidobacterium* spp., *Brevibacterium* spp., *Propionibacterium* spp., *Lactococcus* spp., *Lactobacillus* spp., *Streptococcus* spp., *Enterococcus* spp., *Pediococcus* spp., *Leuconostoc* spp., *Oenococcus* spp., yeast cultures, filamentous fungi, or a combination thereof in an amount of at least $10^9$ colony forming units (CFU) per gram of starter culture and
    (b) a cryoprotective agent selected from the group consisting of inosine 5' monophosphate (IMP), cytidine 5' monophosphate (CMP), or a combination thereof;
        wherein, if the starter culture is non-liquid frozen, the cryoprotective agent is about 0.5% to 20% w/w of the non-liquid frozen starter culture; and
        wherein, if the starter culture is freeze-dried, the cryoprotective agent is about 0.8-60% w/w of the freeze-dried starter culture.

2. The starter culture of claim 1, wherein the cryoprotective agent is inosine-5'-monophosphate (IMP).

3. The starter culture of claim 1 or 2, wherein the cryoprotective agent also has a booster effect.

4. The starter culture of claim 1 or 2, wherein the starter culture is non-liquid frozen and comprises cryoprotective agent from 0.5% to 7% w/w of the non-liquid frozen starter culture.

5. The starter culture of claim 4, wherein the starter culture is non-liquid frozen and comprises cryoprotective agent from 2% to 5% w/w of the non-liquid frozen starter culture.

6. The starter culture of claim 1, wherein the microorganism is a mesophilic culture of *Lactococcus* spp., *Lecuconostoc* spp., *Lactobacillus* ssp., or a combination thereof.

7. The starter culture of claim 6, wherein said mesophilic microorganism is *Lactococcus lactis*, *Lactococcus lactis* subsp. *cremoris*, *Leuconostoc mesenteroides* subsp. *cremoris*, *Pediococcus pentosaceus*, *Lactococcus lactis* subsp. *lactis* biovar *diacetylactis*, *Lactobacillus casei* subsp. *casei*, *Lactobacillus paracasei* subsp. *paracasei*, or a combination thereof.

8. The starter culture of claim 1 or 2, wherein said microorganism is a theromophilic organism.

9. The starter culture of claim 8, wherein said thermophilic organism is *Streptococcus thermophilus*, *Enterococcus faecium*, *Lactobacillus delbrueckii* subsp. *lactis*, *Lactobacillus helveticus*, *Lactobacillus delbrueckii* subsp. *bulgaricus*, *Lactobacillus acidophilus*, or a combination thereof.

10. The starter culture of claim 1, wherein the microorganism is a *Lactococcus* spp.

11. The starter culture of claim 1, wherein the microorganism is a *Lactobacillus* spp.

12. The starter culture of claim 1, wherein the microorganism is a yeast culture or filamentous fungi.

13. The starter culture of claim 1, wherein the microorganism is a *Lactococcus* spp., *Lactococcus lactis* subsp. *lactis*, *Lactococcus lactis* subsp. *cremoris*, or a mixture thereof.

14. The starter culture of claim 11, wherein the microorganism is *Lactobacillus acidophilus*.

15. The starter culture of claim 12, wherein the yeast culture is a *Saccharomyces* spp.

16. The starter culture of claim 1, wherein said starter culture is freeze-dried and the amount of cryoprotective agent ranges from 3% to 30% w/w of freeze-dried starter culture.

17. The starter culture of claim 1, wherein the cryoprotective agent is cytidine 5' monophosphate (CMP).

18. The starter culture claim 12, wherein the filamentous fungi is a *Penicillium* spp., *Cryptococcus* spp., *Debraryomyces* spp., *Klyveromyces* spp., or a mixture thereof.

19. The starter culture of claim 1, wherein the cryoprotective agent further comprises inosine.

20. A stable non-liquid frozen starter culture comprising:
    (a) a microorganism selected from the group consisting of *Bifidobacterium* spp., *Brevibacterium* spp., *Propionibacterium* spp., *Lactococcus* spp., *Lactobacillus* spp., *Streptococcus* spp., *Enterococcus* spp., *Pediococcus* spp., *Leuconostoc* spp., *Oenococcus* spp., yeast cultures, and filamentous fungi, or a combination thereof and
    (b) a cyroprotective agent selected from the group consisting of inosine 5' monophosphate (IMP), cytidine 5' monophosphate (CMP), or a combination thereof;
        wherein the cryoprotective agent is about 0.5% to 20% w/w of the non-liquid frozen starter culture.

21. A stable freeze-dried starter culture comprising:
    (a) a microorganism selected from the group consisting of *Bifidobacterium* spp., *Brevibacterium* spp., *Propionibacterium* spp., *Lactococcus* spp., *Lactobacillus* spp., *Streptococcus* spp., *Enterococcus* spp., *Pediococcus* spp., *Leuconostoc* spp., *Oenococcus* spp., yeast cultures, and filamentous fungi, or a combination thereof and
    (b) a cyroprotective agent selected from the group consisting of inosine 5' monophosphate (IMP), cytidine 5' monophosphate (CMP), or a combination thereof;
        wherein the cryoprotective agent is about by 0.8-60% w/w of the freeze-dried starter culture.

22. The stable non-liquid frozen or freeze-dried starter culture of claim 1, wherein said stable non-liquid frozen or freeze-dried starter culture further comprises inosine.

23. The stable non-liquid frozen starter culture of claim 20, wherein said stable non-liquid frozen starter culture further comprises inosine.

24. The stable freeze-dried starter culture of claim 21, wherein said stable freeze-dried starter culture further comprises inosine.

* * * * *